US011523988B2

(12) United States Patent
Wong et al.

(10) Patent No.: US 11,523,988 B2
(45) Date of Patent: *Dec. 13, 2022

(54) ORAL DISPERSIBLE VACCINE COMPRISING VIROSOMES

(71) Applicants: Catalent U.K. Swindon Zydis Limited, Swindon (GB); Mymetics Corporation, Epalinges (CH)

(72) Inventors: Yik Teng Wong, Wiltshire (GB); Charli Smardon, Wiltshire (GB); Khojasteh Shirkhani, Swindon (GB); Mario Amacker, Schmitten (CH); Sylvain Fleury, Bottens (CH); Antonius Johannes Hendrikus Stegmann, Rijnsburg (NL)

(73) Assignees: Catalent U.K. Swindon Zydis Limited, Swindon (GB); Mymetics Corporation, Epalinges (CH)

( * ) Notice: Subject to any disclaimer, the term of this patent is extended or adjusted under 35 U.S.C. 154(b) by 458 days.

This patent is subject to a terminal disclaimer.

(21) Appl. No.: 16/696,752

(22) Filed: Nov. 26, 2019

(65) Prior Publication Data

US 2020/0170933 A1  Jun. 4, 2020

Related U.S. Application Data

(60) Provisional application No. 62/772,823, filed on Nov. 29, 2018.

(51) Int. Cl.
*A61K 9/00* (2006.01)
*A61K 39/12* (2006.01)
*A61K 39/00* (2006.01)

(52) U.S. Cl.
CPC ............ *A61K 9/006* (2013.01); *A61K 9/0056* (2013.01); *A61K 39/12* (2013.01); *A61K 2039/55555* (2013.01); *A61K 2039/55583* (2013.01)

(58) Field of Classification Search
None
See application file for complete search history.

(56) References Cited

U.S. PATENT DOCUMENTS

| 7,972,621 | B2 | 7/2011 | Wong et al. |
| 9,216,156 | B2 | 12/2015 | Fleury et al. |
| 9,956,169 | B2 | 5/2018 | Tian et al. |
| 2012/0034305 | A1 | 2/2012 | Seager |

FOREIGN PATENT DOCUMENTS

| EP | 2058002 | | 5/2009 |
| EP | 1755666 | | 12/2010 |
| EP | 2477608 | | 10/2014 |
| EP | 2624815 | B1 | 8/2016 |
| EP | 3082769 | | 1/2018 |
| WO | 92/19267 | | 11/1992 |
| WO | 97/13531 | A1 | 4/1997 |
| WO | 2004/071492 | | 8/2004 |
| WO | 2004/110486 | | 12/2004 |
| WO | 2005/117958 | | 12/2005 |
| WO | 2006/045532 | | 5/2006 |
| WO | 2006/069719 | | 7/2006 |
| WO | 2007/068497 | | 6/2007 |
| WO | 2007/099446 | | 9/2007 |
| WO | 2007/107585 | | 9/2007 |
| WO | 2008/008881 | | 1/2008 |
| WO | 2008/042789 | A1 | 4/2008 |
| WO | 2008/080628 | | 7/2008 |
| WO | 2008/152052 | | 12/2008 |
| WO | 2009/000433 | | 12/2008 |
| WO | 2011/124876 | A2 | 10/2011 |
| WO | 2012/041503 | | 4/2012 |
| WO | 2012/158978 | | 11/2012 |
| WO | 2015/059284 | | 4/2015 |
| WO | 2016/009381 | | 1/2016 |
| WO | 2016/039619 | | 3/2016 |
| WO | 2016/039620 | | 3/2016 |
| WO | 2017/047089 | A1 | 3/2017 |

OTHER PUBLICATIONS

International Search Report and Written Opinion dated Mar. 25, 2020, directed to International Application No. PCT/EP2019/082940; 18 pages.
Bomsel et al. (Feb. 2011) "Immunization with HIV-1 gp41 Subunit Virosomes Induces Mucosal Antibodies Protecting Nonhuman Primates against Vaginal SHIV Challenges," Immunity 34; 1-12.
Cusi, M. G. (Jan. 2006). "Applications of Influenza Virosomes as a Delivery System," Human Vaccines 2(1): 1-7.
Czerkinsky et al. (Jan. 2011) "Sublingual Vaccination," Human Vaccines 7(1): 110-114.
Herzog et al. (May 2009) "Eleven Years of Inflexal® V-a Virosomal Adjuvanted Influenza Vaccine," Vaccine 27: 4381-4387.
Kraan et al. (Jun. 2014) "Buccal and Sublingual Vaccine Delivery," Journal of Controlled Release 190: 580-592.
Leroux-Roels et al. (Feb. 2013). "Randomized Phase I: Safety, Immunogenicity and Mucosal Antiviral Activity in Young Healthy Women Vaccinated with HIV-1 Gp41 P1 Peptide on Virosomes," PLOS ONE 8(2): 1-15.

(Continued)

*Primary Examiner* — Brian Gangle
(74) *Attorney, Agent, or Firm* — Morrison & Foerster LLP

(57) ABSTRACT

The present disclosure is directed to oral vaccine dosage forms and processes for producing the oral vaccine dosage forms. The dosage forms include lipid-based vesicles (e.g., virosomes, liposomes) harboring an immunogenic amount of at least one vaccinal target molecule, with or without adjuvant. Specifically, Applicants discovered a combination of the composition of the liquid virosome concentrates, the composition of the base matrix for the solid dosage form formulation (excluding the virosome concentrate), and the manufacturing conditions for the dosage forms that can produce a freeze dried sublingual dosage form having physical robustness, particle and antigen integrity and stability.

40 Claims, 5 Drawing Sheets

(56) References Cited

OTHER PUBLICATIONS

Moser et al. (2013) "Influenza Virosomes as Vaccine Adjuvant and Carrier System," Expert Reviews Vaccines 12(7): 779-791.
Pedersen et al. (Nov. 2011) "Evaluation of the Sublingual Route for Administration of Influenza H5N1 Virosomes in Combination with the Bacterial Second Messenger c-di-GMP," PLOS ONE 6(11): 1-12.

Shim et al. (Jun. 2013) "Sublingual Delivery of Vaccines for the Induction of Mucosal Immunity," Immune Network 13 (3): 81-85.

Smirnov et al. (May 2011) "Vaccine Adjuvant Activity of 3M-052: An Imidazoquinoline Designed for Local Activity Without Systemic Cytokine Induction," Vaccine 29: 5434-5442.

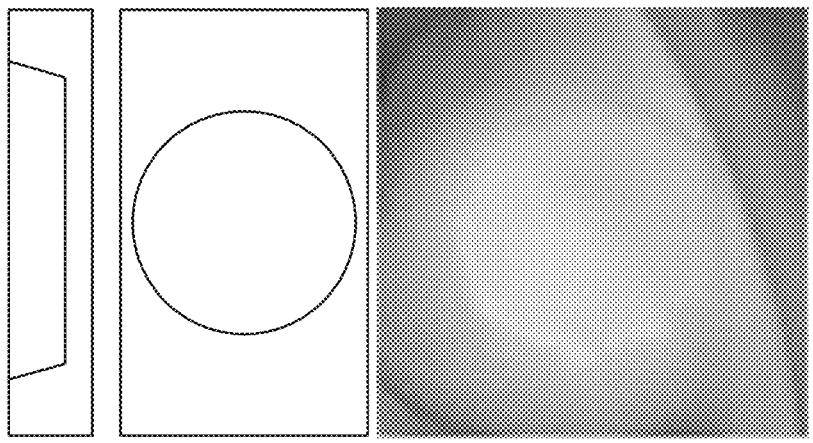
FIG. 3C SKIN REMAINS
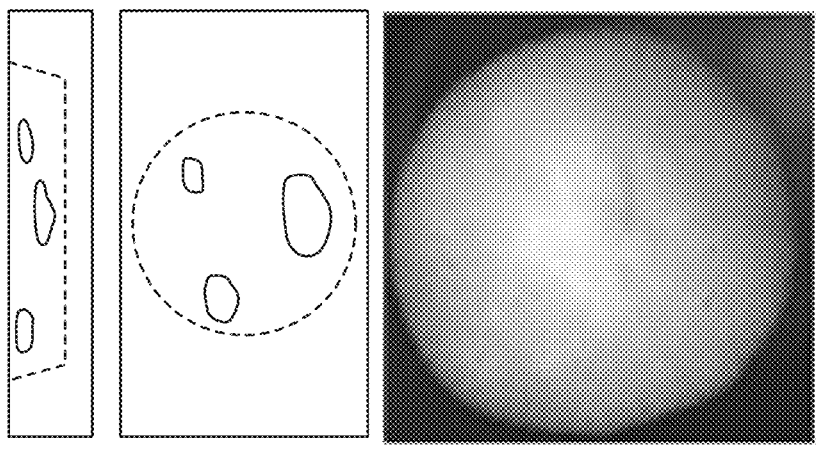
FIG. 3B LUMPS
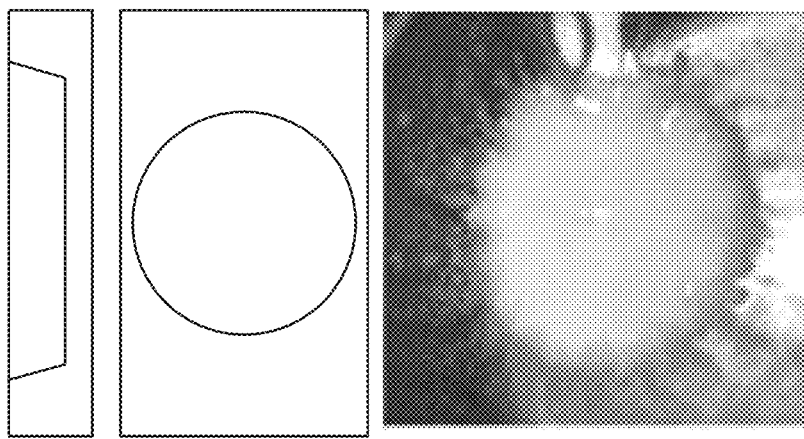
FIG. 3A FULLY WETTED

ORAL DISPERSIBLE VACCINE COMPRISING VIROSOMES

REFERENCE TO RELATED APPLICATIONS

This application claims the benefit of U.S. Provisional Application No. 62/772,823, filed Nov. 29, 2018, the entire contents of which are incorporated herein by reference.

FIELD OF THE INVENTION

This disclosure relates to an oral dosage form that induces mucosal immunization.

More specifically, this disclosure relates to a freeze-dried orally dispersible vaccine containing virosomes. The project leading to this application has received funding from the European Union's Horizon 2020 research and innovation programme under grant agreement No 646122.

BACKGROUND OF THE INVENTION

Vaccines are traditionally delivered by intramuscular, intradermal, or subcutaneous injections. These injections can produce strong systemic immune responses, while the efficacy for triggering mucosal immune responses are variable and often weak or undetectable, particularly for subunit vaccines. From the draining lymph nodes that have processed the injected vaccine, antigen specific cytotoxic T cells (CTLs) and antibodies produced by B cells can migrate to different organs in the body but their migration to the various mucosal tissues (e.g., genital, intestinal, respiratory) is often limited or not possible due to inadequate homing mucosal receptors and chemotaxis. However, the intranasal route that is also considered as a parenteral immunization route can trigger good mucosal immune responses in the respiratory, genital and intestinal tract that are sharing some interconnections, which is more accessible if the vaccine is delivered at the mucosal site. Therefore, such parenteral vaccines may offer protection in some cases against mucosal pathogens.

Because most pathogens enter the body through mucosal tissues (oral, respiratory, genital, and intestinal tracts) and many of them only replicate in the mucosal tissues, mucosal vaccination may optimally induce front line defense by inducing both innate (ex. NK cells) and adaptive (T and B cells) immune responses at the local and distant mucosal sites.

With resident mucosal defense, protection can be immediate with no delay in cell recruitment from the periphery, which allows to interfere more efficiently with very early events of transmission and infection events prior pathogen spreading and in some cases, reservoir establishment.

Mucosal tissues and lymph nodes contain more than 90% of the immune cells. Moreover, mucosal antibodies represent about 80% of the total body antibody production. Thus, the local immune response by mucosal antibodies can act as a front line defense against mucosal infections (e.g., HIV-1, herpes viruses, rotaviruses, etc.) and entry across mucosal tissues for reaching other organs (e.g., HIV-1, hepatitis B, tuberculosis). In contrast, blood antibodies can act as a backup defense once the pathogens have crossed the mucosal defense or in synergy with mucosal antibodies and mucus environment. Blood antibodies primarily act as an efficient front line defense for dealing with pathogens entering directly into the blood stream following mosquito bites (e.g., malaria, chikungunya, dengue, Zika, West Nile virus, yellow fever, etc.) or accidental skin/mucosal injuries (e.g., *Staphylococcus aureus, Pseudomonas aeruginosa*).

Mucosal vaccine delivery (via the buccal, sublingual, nasal, oral, or vaginal mucosa) has received increasing interest as a means of inducing local and distant antibody immune response as well as systemic immune response. In addition, mucosal vaccine delivery by solid dosage forms (e.g., buccal/sublingual tablets, oral tablets or capsules, vaginal inserts) can offer several advantages such as the potential for mass immunization, patient compliance, ease of use, product shelf life stability, cold-chain independent capability. Furthermore, mucosal vaccine delivery can be suitable for patients that have needle injection phobia and the patient can self-administrate the vaccine with adequate explanations. The buccal/sublingual route has been used for many years to deliver drugs and small molecules to the bloodstream, but its application as a means of mucosal delivery for vaccines has received little attention.

BRIEF SUMMARY OF THE INVENTION

Lipid-based vesicles can be used as drug, vaccine, or adjuvant delivery systems, and combinations of thereof. Lipid-based vesicles can consist of one or several natural and/or synthetic lipids forming the base structure (particle) and additional optional components (peptides, proteins, carbohydrates, nucleic acids, small molecules). Lipid-based vesicles can range from the nanoparticle (approximately 20-200 nm) to the sub-micrometer (approximately 200-800 nm) to the micrometer (approximately 800 nm-10 μm) scale.

Virosomes and liposomes belong to the lipid-based vesicle systems. Virosomes are unilamellar, and liposomes can be unilamellar, bilamellar, or multilamellar. Virosomes are a type of subunit vaccine that may contain any enveloped virus derived protein that is used as starting material for the formation of the lipid-based virosome particles. These virosomes can be devoid of genetic material, non-replicative and not infectious, which makes them suitable and safe for enteral and parenteral immunization, provided that they can be formulated in a stabilized form. Virosomes may contain additional molecules such as homologous (same pathogen origin) or heterologous target molecules (derived from a pathogen different from the starting virus material) under peptide, protein, and/or carbohydrate forms, nucleic acids, adjuvants, specific lipids and/or small molecules (drugs). Similar to virosomes, liposomes can also be used as a vehicle for administration of pharmaceutical drugs, vaccines, and adjuvants, but the lipid membrane does not contain any native viral proteins. In some embodiments, the liposomes used herein can be proteoliposomes (i.e., liposomes with proteins).

Ideally, stabilization would either permit the vaccine storage independent of the cold chain or allow the vaccine to support high and low temperature excursions outside the recommended cold chain conditions without compromising the bioactivity of the product.

Applicants have discovered a freeze dried oral dispersible vaccine containing virosomes and the process of making such a vaccine that can preserve the stability of the virosomes (both physically for the particle structure and chemically for the target molecules). The product stability can be maintained during storage at ambient temperature (e.g., about 25° C.), independent of the cold chain storage conditions, and may also support accidental freezing conditions (e.g., −about 4° C. to about −17° C.) as well as exposure to high temperatures present in warm countries (e.g., 35° C. to 45° C.). The freeze dried sublingual dosage forms disclosed herein that contain the virosomal vaccine can induce mucosal immunity, and may also elicit systemic immune responses. Specifically, the combination of the composition of the liquid virosome concentrate and its buffer, the composition of the liquid base matrix for solid dosage form (excluding the virosome concentrate), and the manufacturing conditions for generating solid dosage forms under freeze dried sublingual tablets can generate a solid vaccine form that has proper physical attributes for sublingual tablets, with preserved virosomes and target molecule integrity, harboring stability during storage under different environmental conditions. Administering stable virosome solid dosage forms can be suitable for sublingual mucosal immunization.

Virosomes belong to the enveloped virus like particle ("VLP") family, as they have lipid membranes containing viral membrane proteins derived from the starting purified viruses. As VLPs, virosomes can closely mimic the virus particle architecture, composition, antigen membrane surface presentation, with or without functional activities of the native viral envelope. Virosomes may comprise reconstituted viral membranes, generally obtained by purification of solubilized membrane proteins and lipids from enveloped viruses with solubilization agent, followed by addition of natural or synthetic lipids and antigens, with or without adjuvants, and removal of said solubilization agent from the mixture, leading to lipid bilayer formation with the proteins protruding from them. Antigens can be native proteins as well as recombinant or synthetic proteins or peptides. Virosomes may also be formed first, and then modified by the covalent or non-covalent modification of their membranes to contain adjuvants and other molecules. A characteristic feature of virosomes is that they can closely mimic the composition, surface architecture and functional activities of the native viral envelope. In some cases, when the induction of CD8+ T cells is part of the vaccine strategy, a particularly important characteristic of said virosomes is the preservation of the hemagglutinin (HA) receptor-binding with its fusion membrane activity. If the vaccine strategy focuses on the induction of antigen specific antibodies, then the HA fusion activity is not absolutely required but the presence of HA as excipient is still important, as it can provide T cell help, particularly for small antigens and peptides that maybe devoid of such properties. Although specific vaccines are mentioned in this disclosure, all vaccines that use virosomes as a delivery platform are contemplated by this disclosure. Influenza virosome containing HIV antigens (P1 and rgp41) and TLR 7/8 adjuvant can be used as model virosome concentrates for the vaccines disclosed herein. The influenza virosomes with HIV antigen rgp41 have been shown to be capable of eliciting immune responses in various animal studies and in a Phase 1 clinical study via the intranasal and intramuscular route. In such studies, the virosome formulations were under liquid form administered by needle or nasal liquid spray, which were susceptible to show limited shelf life stability at 4° C. due to chemical modifications of the Active Pharmaceutical Ingredients ("APIs"). To prevent or reduce such API chemical modifications often present in aqueous environments, developing solid vaccine forms with low moisture content was identified as a promising approach.

Applicants were able to overcome various problems in producing a solid vaccine form as the freeze dried oral dispersible vaccines disclosed herein. Specifically, the influenza-based virosome concentrates that contain the virosomes carrying antigens and adjuvants may be supplied as a suspension in a buffer salt solution. To produce the freeze dried vaccine dosage forms, robust and porous structures within the tablets should be produced during manufacture and sustained during subsequent storage. The presence of buffer salts in the virosome concentrates can present a challenge in the manufacture of such a robust and porous structure. As such, Applicants discovered an appropriate amount of excipients in conjunction with manufacturing conditions to enable the formation of a robust dosage form that does not collapse or partially collapse during the freeze drying process.

In addition, the freezing, annealing, and freeze drying process may also damage the integrity of the virosome particles. This damage to the virosomes should be minimized such that sufficient virosome particles remain in the freeze dried product such that a sufficient amount of them can cross the sublingual mucosal membrane for being processed by the immune cells to induce mucosal immune responses, that maybe also supported by a systemic immune responses. As such, Applicants were able to balance the excipient usage and freeze drying process to maintain both the virosome immunogenicity (e.g., intact virosomes with limited presence of clusters) and good dosage form properties (e.g., orally disintegrating sublingual tablets).

In some embodiments, an oral solid vaccine dosage form includes lipid-based vesicles comprising an immunogenic amount of at least one target molecule; 5-20 wt. % of at least one cryo-lyoprotectant; 25-40 wt. % of a matrix former; and 40-55 wt. % of a structure former. In some embodiments, the lipid-based vesicles are virosomes or proteoliposomes. In some embodiments, the dosage form comprises 10-15 wt. % of at least one cryo-lyoprotectant. In some embodiments, the at least one cryo-lyoprotectant comprises trehalose. In some embodiments, the dosage form comprises 33-37 wt. % of the matrix former. In some embodiments, the matrix former comprises gelatin. In some embodiments, the gelatin comprises fish gelatin. In some embodiments, the fish gelatin is high molecular weight fish gelatin. In some embodiments, the dosage form comprises 45-50 wt. % of the structure former. In some embodiments, the structure former comprises mannitol. In some embodiments, the virosomes are derived from the influenza virus membrane or other enveloped viruses. In some embodiments, the at least one target molecule is present on the virosome. In some embodiments, the at least one target molecule comprises an HIV-1 envelope derived antigen. In some embodiments, the HIV-1 envelope derived antigen comprises HIV-1 PI peptide and/or HIV-1 recombinant gp41. In some embodiments, the virosomes comprise adjuvant. In some embodiments, the dosage form facilitates oral cavity uptake of the at least one target molecule. In some embodiments, the dosage form disintegrates within 180 seconds after being placed in the oral cavity. In some embodiments, the dosage form disintegrates within 90 seconds after being placed in the oral cavity. In some embodiments, the dosage form disintegrates within 60 seconds after being placed in the oral cavity. In some embodiments, the dosage form disintegrates within 30 seconds after being placed in the oral cavity. In some embodiments, an immune response is induced when administered to a patient by placement in the oral cavity. In some embodiments, placement in the oral cavity is placement on or under the tongue or in the buccal or pharyngeal region.

In some embodiments, a method of inducing an immune response in a patient includes placing any of the dosage forms above in an oral cavity of a person in need of the immune response. In some embodiments, placement in the oral cavity is placement on or under the tongue or in the buccal or pharyngeal region.

In some embodiments, a method of forming an oral solid vaccine dosage form includes dosing a liquid virosome formulation into a preformed mold, wherein the virosome formulation comprises: lipid-based vesicles comprising an immunogenic amount of at least one target molecule, 1-5 wt. % a cryo-lyoprotectant, 4-8 wt. % of a matrix former, and 5-10 wt. % of a structure former; freezing the dosed virosome formulation at a temperature of −60° C. to −90° C.; annealing the frozen virosome formulation by holding it at a temperature of less than −15° C. for 3-9 hours; and freeze-drying the annealed virosome formulation to form the dosage form. In some embodiments, the dosed virosome formulation is frozen at a temperature of −60° C. to −90° C. for a duration of about 1-5 minutes. In some embodiments, freeze-drying the annealed virosome formulation comprises a first step of holding the annealed virosome formulation at a temperature of −10° C. to −20° C. for 20-28 hours and a second step of holding the annealed virosome formulation at a temperature of −5° C. to about −15° C. for 14-22 hours. In some embodiments, the freeze-drying occurs at a pressure of less than 600 mbar. In some embodiments, the virosome formulation has a pH of about 6.5-8. In some embodiments, the cryo-lyoprotectant comprises trehalose. In some embodiments, the matrix former comprises gelatin. In some embodiments, the gelatin comprises fish gelatin. In some embodiments, the fish gelatin is high molecular weight fish gelatin. In some embodiments, the structure former comprises mannitol. In some embodiments, the lipid-based vesicles are derived from the influenza virus or respiratory syncytial virus. In some embodiments, the at least one target molecule comprises an HIV-1 envelope derived antigen. In some embodiments, the HIV-1 envelope derived antigen comprises HIV-1 PI peptide or HIV-1 recombinant gp41. In some embodiments, the lipid-based vesicles comprise adjuvant.

In some embodiments, a method of forming an oral solid vaccine dosage form includes: dosing a liquid virosome formulation into a preformed mold, wherein the virosome formulation comprises: (1) 20-50 wt. % of a virosome concentrate, wherein the virosome concentrate comprises: virosomes comprising an immunogenic amount of at least one target molecule; 2-10 wt. % of a cryo-lyoprotectant; and 60-200 mM of a buffer system; (2) 4-8 wt. % of a matrix former; and (3) 5-10 wt. % of a structure former; freezing the dosed virosome formulation at a temperature of −60° C. to −90° C.; annealing the frozen virosome formulation by holding it at a temperature of less than −15° C. for 3-9 hours; freeze-drying the annealed virosome formulation to form the dosage form. In some embodiments, the buffer system comprises HEPES-Sodium Chloride.

Additional advantages will be readily apparent to those skilled in the art from the following detailed description. The examples and descriptions herein are to be regarded as illustrative in nature and not restrictive.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

BRIEF DESCRIPTION OF THE DRAWINGS

Exemplary embodiments are described with reference to the accompanying figures, in which:

FIG. 3A is a schematic representation with a picture of a fully wetted tablet.

FIG. 3B is a schematic representation with a picture of a tablet with hard lumps.

FIG. 3C is a schematic representation with a picture of a tablet with a film of collapsed formulation matrix that forms at the surface of the freeze dried tablet (skin).

DETAILED DESCRIPTION OF THE INVENTION

Figure 1:
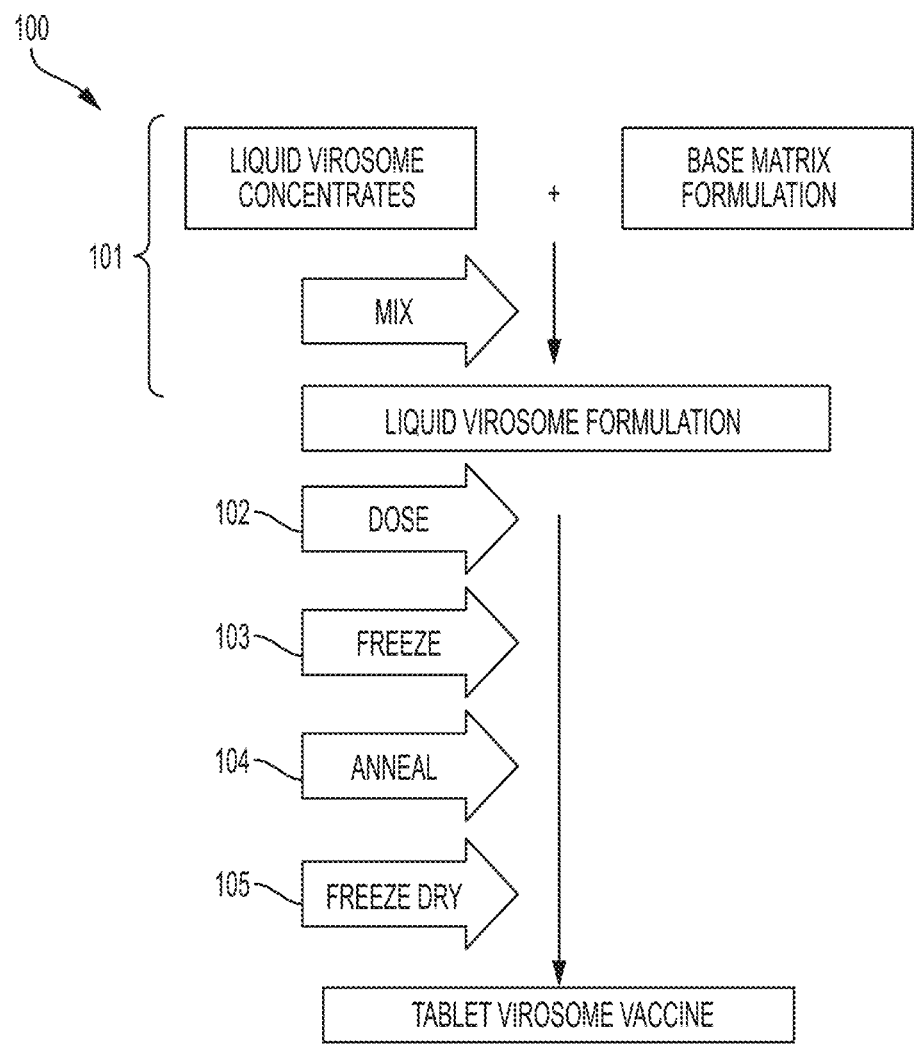
FIG. 1 illustrates a flow chart overview for producing a vaccine dosage form disclosed herein.

Disclosed herein are pharmaceutical compositions for lipid-based vesicles (e.g., virosomes or VLPs) and methods of preparing these pharmaceutical compositions. Specifically, the present disclosure relates to freeze dried orally dispersible or disintegrating dosage forms that can preserve the stability of the VLPs (i.e., structural integrity and antigen chemical stability), can be stored independent of cold chain storage conditions and can also support accidental freezing conditions as well as exposure to high temperatures present in warm countries. The dosage forms can also retain the VLP's physical and chemical attributes making it suitable for sublingual delivery to induce mucosa immunization.

Applicants were able to formulate and optimize the amount of matrix former and structure former to have a formulation that can address the use of a high loading of a virosome concentrates containing buffer systems and cryo-lyoprotectants. In conjunction with the excipient adjustments, the manufacturing parameters of the dosage forms were optimized. Specifically, the annealing time was optimized to maximize the mannitol crystallization that imparts dosage form robustness and minimize the virosome damage. In addition, the freeze-drying conditions were optimized to minimize damage to the virosome particles as well as minimize structural collapse during freeze-drying.

Lipid Based Vesicle Systems

Lipid-based vesicles can be used as drug, vaccine, or adjuvant delivery systems, and combinations of thereof. Lipid-based vesicle systems can consist of one or several natural and/or synthetic lipids (ex. phosphatidylethanolamine, phosphatidylcholine, phosphatidylserine, phosphatidylinositol, phosphatidylglycerol, cholesterol, sphingolipids and their derivatives) forming the vesicle membrane (particle) and additional optional components (peptides, proteins, carbohydrates, small molecules). Lipid-base vesicles range from the nanoparticle (about 20-200 nm) to the sub-micrometer (about 200-800 nm) to the micrometer (about 800 nm-10 μm) scale.

A lipid-based vesicle/particle may comprise a unilamellar, bilamellar, or a multilamellar lipid bilayer vesicle. In some embodiments, a lipid-based vesicle/particle can include a lipid bilayer comprising lipids chosen from natural and/or synthetic lipids. Such lipids may be used to better mimic the pathogen membrane and lipid raft microdomains in order to improve antigen membrane anchorage, antigen presentation, and/or folding for optimal epitope exposure. The lipid-based vesicle/particle may harbour membrane anchored antigen and/or adjuvant exposed at the surface of the particle or pointing toward inside the particle or having a random orientation. Antigen and/or adjuvant can also be encapsulated inside the lumen of the lipid-based vesicle/particle.

Virosomes are lipid-based vesicles in vitro assembled, in a cell-free system manner, forming enveloped VLPs that belong to the subunit vaccine category. Virosome lipid membranes as carrier can be derived from any enveloped virus and consequently, contain at least native viral membrane proteins from the starting virus. These virosomes are devoid of genetic viral material, can't replicative and are not infectious, which makes them suitable and safe for systemic and mucosal immunization. In addition, virosomes may contain additional molecules such as antigens (e.g. peptides, proteins, carbohydrates, nucleic acids), adjuvants, specific lipids and/or small molecules (drugs), which can be anchored at the virosomes surface and/or entrapped inside the virosome lumen.

Liposomes are also lipid-based vesicles forming a type of subunit vaccine that can be formed as vesicles having at least one lipid bilayer, which don't contain proteins derived from natural viral membrane of enveloped viruses. Such lipid-based particles also in vitro assembled are devoid of genetic material and can be suited for systemic and mucosal application. In addition, liposomes may contain additional molecules such as antigens (peptides, proteins and/or carbohydrates, nucleic acids), adjuvants, specific lipids and/or small molecules (drugs), which can be anchored at the liposome surface and/or entrapped inside the liposome lumen. In some embodiments, the liposomes used herein can be proteoliposomes (i.e., liposomes with proteins).

The lipids used in the dosage forms described herein can belong to the cationic lipids, glycolipids, phospholipids, glycerophospholipids, galactosylceramid, sphingolipids, cholesterol and derivatives thereof. Phospholipids may include, but are not limited to, phosphatidylcholine, sphingomyelin, phosphatidylethanolamine, phosphatidylserine, phosphatidylglycerol, phosphatidic acid, cardiolipin, and phosphatidylinositol with varying fatty acyl compositions.

In addition, lipids may be chosen from DOTMA (N-[1-(2,3-dioleylaxy)propyl]-N,N,N-trimethylammonium chloride), DOTAP (N-[1-(2,3-dioleoyloxy)propyl]-N,N,N-trimethylammonium chloride, DODAC (N,N-dioleyl-N,N,-dimethylammonium chloride), DDAB (didodecyldimethylammonium bromide) and stearylamine or other aliphatic amines and the like.

Virosome Formulation
Virosome Concentrate

FIG. 1 illustrates a flow chart for a method 100 of producing a vaccine dosage form disclosed herein. At step 101, a liquid virosome concentrate can be mixed with a premixture of base matrix formulation to form a liquid virosome formulation suitable for freeze-drying. Applicants have found that when a composition of a virosome concentrate is combined with a specific composition of a base matrix formulation and prepared in conjunction with a set of manufacturing conditions optimized to preserve sufficient virosomes with the required particle characteristics, the vaccine bioactivity can be maintained. The bioactivity of the virosome particles can be dependent on the conformational integrity of the particles and quality of the antigenic molecules that are associated with its unilamellar phospholipid membrane.

In some embodiments, the virosome concentrate can be a liquid virosome concentrate. The virosome concentrate includes at least one virosome population. A virosome population can be virosomes containing a given drug, or virosomes acting as vaccine delivery vehicle harboring vaccinal antigens and virus derived proteins (e.g., HA if the virosomes are derived from influenza virus).

In some embodiments, the virosomes can be derived from an influenza virus for generating influenza virosomes as enveloped VLPs acting as carrier for heterologous vaccinal antigens (ex. HIV antigens anchored on influenza derived virosomes) or from another enveloped virus like the respiratory syncytial virus ("RSV"), In some embodiments, the enveloped viruses like the RSV, the Sendai virus, Semliki Forest virus (SFV), vesicular stomatitis virus (VSV), or Sindbis can be used for generating the corresponding RSV-virosomes, Sendai-virosomes, SFV-virosomes, VSV-virosomes or Sindbis-virosome for homologous vaccinal antigen displayed (ex. native RSV antigens on virosomes derived from RSV). In some embodiments, the virus based virosomes can be derived from any enveloped virus. In some embodiments, the virus based virosomes can be derived from DNA viruses including, but not limited to, Herpesviruses, Poxyviruses, and Hepadnaviruses. In some embodiments, the virus based virosomes can be derived from RNA viruses including, but not limited to, Flavivirus, Togavirus, Coronavirus, Hepatitis D, Orthomyxovirus, Paramyxovirus, Rhabdovirus, Bunyavirus, and Filovirus. In some embodiments, the virus based virosomes can be derived from retroviruses.

In some embodiments, an influenza virus based virosome can be formed according to the different processes described in *Influenza virosomes as vaccine adjuvant and carrier system*; Moser C. et al, Expert review, 779-791 (2013); WO2004110486; WO2004071492; WO2007099446; WO2016039619; EP2058002; and WO2016039620, which are hereby incorporated herein by reference in their entirety. In addition, the various patents and other publications listed in the previously cited references are also incorporated herein by reference in their entirety. As such, this application is not limited to a specific process for virosome preparation. As such, the reference described above is simply an example of virosome preparation. This application applies to all lipid-based particles such as but not limiting to virosomes, VLPs, and nanoparticle preparation, including liposomes with antigens.

Although this section describes a liquid virosome concentrate, the virosome can be replaced with a liposome to form a liquid liposome concentrate. As such, the components in the virosome concentrate (besides the virosomes themselves) can equally be applied to a liposome concentrate.

The virosome (e.g., influenza derived virosome) can have viral proteins on its surface. In some embodiments, the protein can be hemagglutinin ("HA") and/or neuraminidase ("NA"). In some embodiments, the liquid virosome concentrate includes viral membrane proteins (e.g. HA) present in a concentration detectable by state of the art analytical assays. In some embodiments, the viral membrane proteins are about 10-300 µg/mL or about 5-150 µg/mL of the liquid virosome concentrate, when using influenza virosomes as carrier of heterologous vaccinal antigens. For influenza virosomes designed for inducing CTL responses, the HA concentration can range at about 150-800 µg/mL or about 75-400 µg/mL. In some embodiments the concentration of viral membrane proteins can be greater than the example concentrations listed above.

The virosome concentrate can also include lipids. The lipids used in the virosome concentrate can belong to the cationic lipids, glycolipids, phospholipids, glycerophospholipids, galactosylceramid, sphingolipids, cholesterol and derivatives thereof. Phospholipids may include, in particular, phosphatidylcholine, sphingomyelin, phosphatidylethanolamine, phosphatidylserine, phosphatidylglycerol, phosphatidic acid, cardiolipin, and phosphatidylinositol with varying fatty acyl compositions. In addition, lipids may be chosen from DOTMA (N-[1-(2,3-dioleylaxy)propyl]-N,N,N-trimethylammonium chloride), DOTAP (N-[1-(2,3-dioleoyloxy)propyl]-N,N,N-trimethylammonium chloride, DODAC (N,N-dioleyl-N,N,-dimethylammonium chloride), DDAB (didodecyldimethylammonium bromide) and stearylamine or other aliphatic amines and the like. In some embodiments, the liquid virosome concentrate can include about 0.1-10 mg/mL, about 0.3-8 mg/mL, or about 0.5-5 mg/mL of lipids.

The virosomes can contain target molecules (e.g., vaccinal antigens) with or without adjuvants. Antigens can be soluble and entrapped inside the virosome lumen or covalently or non-covalently anchored on virosomes, which can be peptides, proteins, polysaccharides, whole or partial fragments or extracts of bacterial cells, viral particles, or nucleic acids, or can be derived from a parasite, such as a protozoan or worm, which causes disease, or combinations thereof, or derived from any plant, animal or human cells or cell lines. Any antigen known in the art can be suitable for use with the virosomes, including those commercially available, or made by purification of preparations of a pathogen or cancer cell or non-transformed cell (native proteins), recombinantly expressed, or produced synthetically by standard manufacture. Methods for generating suitable antigens for incorporation into the virosomes are known in the art, and any of the known methods may be used as disclosed herein.

The target molecule(s) is included in the virosomes of the liquid virosome concentrate and in the subsequent dosage forms disclosed herein in an amount, which is sufficient to render it immunogenic when provided in a dosage form. The "immunogenic amount" is defined as the amount appropriate to provoke a desired immune response. A person of skill in the art can readily determine the immunogenic amount for a given disease or infection based on, among other facts, route of immunization, age and weight of the patient to whom the dosage form will be administered.

In some embodiments, the liquid virosome concentrate may include about 1-2000 µg/mL of target molecule. The target molecule may be a peptide, a protein, a carbohydrate, a nucleic acid, or a small molecule, or a combination thereof. The target molecule may function as an antigen (e.g., vaccinal antigen), a drug, a diagnostic molecule, an analytical sensor, or a combination thereof. In some embodiments, the liquid virosome concentrate can include about 1-1000 µg/mL of one target molecule and about 1-1000 µg/mL, of a second target molecule. After downstream processing into solid dosage forms, each tablet may contain about 0.01 to 250 µg of each target molecule.

In more preferred embodiments, the liquid virosome concentrate may include about 25-500, about 50-500 µg/mL, about 25-225 µg/mL, about 25-200 µg/mL, about 50-450 µg/mL, about 50-400, about 100-400 µg/mL, about 100-400 µg/mL, about 100-200 µg/mL, or about 200-400 µg/mL of at least one target molecule (e.g., antigen). In some embodiments, the liquid virosome concentrate can include about 1-500 µg/mL, about 25-500 µg/mL, about 50-450 µg/mL, about 50-400 µg/mL, about 25-250 µg/mL, about 25-200 µg/mL, about 50-250 µg/mL, about 75-225 µg/mL, or about 100-200 µg/mL of one target molecule and about 50-450 µg/mL, about 50-400 µg/mL, about 25-225 µg/mL, about 25-200 µg/mL, about 100-500 µg/mL, about 150-450 µg/mL, about 175-425 µg/mL, or about 200-400 µg/mL of a second target molecule.

The dosage forms disclosed herein can be used to deliver therapeutic or prophylactic vaccines to prevent or reduce symptoms related to allergies or infection, tumor development and spreading, pathogen transmission, cell infection, pathogen load, after induction of B cells (antibodies) and/or relevant T cell subsets (ex, Th1, Th2, Th16, Thf, Tc1, Tc2, Tc3, Treg, others), which depends on the virosome formulations. To that end, the target molecules can provide protection against the following representative list of diseases which is not exhaustive: influenza, tuberculosis, meningitis, hepatitis, whooping cough, polio, tetanus, diphtheria, malaria, cholera, herpes, typhoid, HIV/AIDS, measles, lyme disease, travellers' diarrhea, hepatitis A, B and C, otitis media, dengue fever, rabies, parainfluenza, rubella, yellow fever, dysentery, legionnaires disease, toxoplasmosis, q-fever, hemorrhagic fever, Argentina hemorrhagic fever, caries, chagas disease, urinary tract infection caused by *E. coli*, pneumoccoccal disease, mumps, chikungunya, cancer, allergies, and combinations thereof. In addition, the target molecules may provide protection against disease caused by the following, non-exhaustive list of causative organisms: *Vibrio* species, *Salmonella* species, *Bordetella* species, *Haemophilus* species, *Toxoplasmosis gondii*, Cytomegalovirus, *Chlamydia* species, Streptococcal species, Norwalk Virus, *Escherischia coli, Helicobacter pylori*, Rotavirus, *Neisseria gonorrhae, Neisseria meningiditis*, Adenovirus, Epstein Barr virus, Japanese Encephalitis Virus, *Pneumocystis carini*, Herpes simplex, *Clostridia* species, Respiratory Syncytial Virus, *Klebsiella* species, *Shigella* species, *Pseudomonas aeruginosa*, Parvovirus, *Camylobacter* species, *Rickettsia* species, *Varicella zoster, Yersinia* species, Ross River Virus, J. C. Virus, *Rhodococcus equi, Moraxella catarrhalis, Borrelia burgdorferi, Pasteurella haemolytica*, and combinations thereof. In addition or alternatively, the target molecule may provide protection or treatment against allergies (i.e., virosomes containing allergens), cancer (e.g., tumor antigens, antibodies, anti-cancer drugs, nucleic acid), and other types of conditions.

Veterinary applications of the present disclosure are also contemplated. Accordingly, the target molecules can provide protections against the following non-exhaustive list of veterinary diseases: coccidiosis, Newcastle disease, enzootic pneumonia, feline leukemia, atrophic rhinitis, erysipelas, foot and mouth disease, swine, pneumonia, and other disease conditions and other infections affecting companion and farm animals, and combinations thereof.

In some embodiments, the virosome contains at least one vaccinal antigen in addition to the viral proteins present in the reconstituted membrane. In some embodiments, the vaccinal antigen can be HIV-1 P1 peptide and/or HIV-1 recombinant gp41.

As stated above, the virosomes of the liquid virosome concentrate may also contain, or be admixed with, an adjuvant. Virosomes and other subunit vaccines may require an adjuvant for improving the immune response, resulting in accelerated and enhanced production of antibodies and T cells, while sustaining also the immunological memory. To be effective, it is preferable to have an immune response associated with the generation of a memory response that provides long lasting protection from the specific disease. The adjuvant also can allow to lower the antigen dose (dose sparing) and increase the breadth of the desired immune response. Once exposed to the antigens, the immune system can "remember" it and during re-exposure, the immune response is much faster. The effectiveness of an adjuvant to enhance an immune response can be independent from the antigen with which it is being combined, as adjuvant alone can trigger unspecific immune responses and may lead to autoimmune side effects if strong cell activation is achieved in the absence of antigen. However, when the antigen and adjuvant are physically link together, they all can co-migrate to the same site upon injection, which favors antigen specific immune activation with lower unspecific inflammatory responses. Suitable adjuvants include, but are not limited to: Toll-like receptor (TLR) agonists, inflammasome agonists, nucleotide-binding and oligomerization domain (NOD)—like receptors (NLRs) agonists, more specifically non-toxic bacterial fragments, cholera toxin (and detoxified forms and fractions thereof), chitosan, heat-labile toxin of E. coli (and detoxified forms and fractions thereof), lactide/glycolide homo.+−.and copolymers (PLA/GA), polyanhydride, e.g., trimellitylimido-L-tyrosine, DEAE-dextran, saponins complexed to membrane protein antigens (immune stimulating complexes—ISCOMS), bacterial products such as lipopolysaccharide (LPS) and muramyl dipeptide, (MDP), liposomes, cochleates, proteinoids, cytokines (interleukins, interferons), genetically engineered live microbial vectors, non-infectious pertussis mutant toxin, neurimidase/galactose oxidase, and attenuated bacterial and viral toxins derived from mutant strains, and combinations thereof. A suitable amount of an adjuvant can be readily determined by one of ordinary skill in the art.

In some embodiments, the virosomes can harbor the adjuvant 3M-052 (a TLR7/8 agonist supplied by 3M). In some embodiments, the liquid virosome concentrate may contain 3M-052 adjuvant in the range of about 8-140 µg/mL, about 4-70 µg/mL, about 1-60 µg/mL, and 0.01 to 16 µg per tablet.

In some embodiments, the liquid virosome concentrate can include at least two different virosome populations, each harboring at least one antigen with or without adjuvant. In some embodiments, these two different virosome populations can have different antigens, but the same adjuvant (e.g. virosome-P1/3M-052 mixed with virosomes-rgp41/3M-052). In some embodiments, these two different virosome populations can have different antigens, but with different adjuvant (e.g. virosome-P1/Adjuvant A mixed with virosomes-rgp41/Adjuvant B).

In some embodiments, the virosome concentrate can include at least two different antigens per virosome, with or without adjuvant (e.g. virosome harboring both P1 and rgp41 antigens, with or without adjuvant).

The liquid virosome concentrate can also include a buffer system. In some embodiments, the virosomes can be suspended in the buffer system. The buffer system can maintain the physical integrity and chemical stability of the virosomes in the virosome concentrate. In some embodiments, the virosomes are suspended in a buffer system to maintain a target pH of about 6-9, about 6.5-8, about 7-8, about 7.2-7.6, about 7.3-7.5, or about 7.4. In addition, the buffer system can stabilize the virosomes when it is in a liquid form at storage temperature of about 2-8° C.

Suitable buffer system include, without limitation, HEPES-Sodium Chloride (HN) buffers, HEPES-Sodium Chloride-EDTA (HNE) buffers, phosphate buffer systems (PBS), or combinations thereof. In some embodiments, the buffer system can be about 5-1000 mM, about 60-200 mM, about 100-300 mM, about 125-275 mM, about 150-250 mM, about 175-225 mM about 180-210 mM, about 185-200 mM, about 185-195 mM, or about 190-195 mM in the virosome concentrate. If the buffer system is HEPES-Sodium Chloride in the virosome concentrate, the sodium chloride can be about 5-1000 mM, about 50-150 mM, about 125-175 mM, about 130-160 mM, about 130-150 mM, about 135-145 mM, or about 140-145 mM in the virosome concentrate. If the buffer system is HEPES-Sodium Chloride in the virosome concentrate, the HEPES can be about 1-200 mM, about 10-75 mM, about 10-50 mM, about 25-75 mM, about 30-70 mM, about 40-60 mM, about 45-55 mM, or about 48-52 mM in the virosome concentrate.

The liquid virosome concentrate can also include at least one cryo-lyoprotectant. Virosomes can be damaged during the freezing and/or freeze drying steps of producing the dosage forms disclosed herein. As such, a cryo-lyoprotectant can be included into the virosome concentrate to improve virosome preservation during the freezing and/or freeze drying steps. Examples of cryo-lyoprotectants include, but are not limited to, polyols such as trehalose, sugars such as sucrose, and amino acids such as lysine, oligosaccharides such as inulin (a medium chain oligosaccharide), or combinations thereof. The cryo-lyoprotectants used can be inert to be suitable for vaccine formulation. The liquid virosome concentrate can include about 1-20% w/w, about 1.5-10% w/w, about 2-10% w/w, about 4-10% w/w, about 2-9% w/w, about 2-5% w/w, about 3-8% w/w, about 3.5-8% w/w, about 3.5-7% w/w, about 4-8% w/w, or about 5-7% w/w the cryo-lyoprotectant.

The virosome concentrate can be about 1-75% w/w, about 10-65% w/w, about 15-60% w/w, about 20-55% w/w, about 20-50% w/w, or about 25-50% w/w of the virosome formulation. In some embodiments, the virosome concentrate can be about 15-35% w/w, about 20-30% w/w, about 23-27% w/w, or about 25% w/w of the virosome formulation.

Base Matrix Formulation

The base matrix formulation is what helps provide the structure of the final dosage form. As such, the base matrix formulation can include a matrix former. The matrix former can provide the network structure of the dosage form that imparts strength and resilience during handling. Suitable matrix formers can include, without limitation, gelatin, starch, or combinations thereof. Additional matrix formers can be found in EP 2624815 B 1, which is herein incorporated by reference in its entirety. The gelatin can be fish gelatin, bovine gelatin, porcine gelatin, or combination thereof. Each of the gelatins can have different gelling characteristics. The extent a gelatin solution forms a gel can dependent on the concentration of the gelatin and the temperature of the gelatin solution. A solution of bovine gelatin tends to gel at temperatures of less than 18° C. and thus can be considered a gelling gelatin. In contrast, fish gelatin can remain in solution at temperatures as low as 10° C. and thus can be considered a non-gelling gelatin. In some embodiments, the gelatin can be a low endotoxin gelatin such as one sourced or one produced according to the process disclosed in Provisional Application No. 62/640, 394, which is hereby incorporated by reference in its entirety. In some embodiments, the amount of matrix former in the virosome formulation can be about 1-15% w/w, about 2-12, about 3-10% w/w, about 4-8% w/w, about 4-6%, about 5-7% w/w, or about 6% w/w.

The temperature at which the virosome formulation is dosed can be as low as 10-18° C. As such, a formulation using bovine gelatin alone may not be dosed at these low temperatures. However, a combination of bovine gelatin and another type of gelatin (e.g., fish gelatin) can be used.

Applicants discovered that fish gelatin can provide a freeze-dried tablet with robust matrix structure and a disintegration time of about 30-180 or 30-60 seconds that is desirable to impact sufficient contact time with the oral mucosa. In addition, the fish gelatin can provide freeze dried dosage forms of good physical attributes for formulation compositions that contain a high loading of soluble component like buffer salts, such as the amounts disclosed herein.

In some embodiments, the fish gelatin can be high molecular weight fish gelatin, standard molecular weight fish gelatin, or combinations thereof. High molecular weight fish gelatin is defined as a fish gelatin in which more than 50% of the molecular weight distribution is greater than 30,000 Daltons. Standard molecular weight fish gelatin is defined as fish gelatin in which more than 50% of the molecular weight distribution is below 30,000 Daltons.

In some embodiments, the matrix former can also serve as a stabilizer for the antigens as well as a muco-adhesive. In addition, starch can also serve as an immune-stimulant excipient.

The base matrix formulation can also include a structure former. Suitable structure formers can include sugars including, but not limited to, mannitol, dextrose, lactose, galactose, cyclodextrin, or combinations thereof. The structure former can be used in freeze drying as a bulking agent as it crystallizes to provide structural robustness to the freeze-dried product. Soluble excipients such as buffer salts and trehalose in the virosome formulation can inhibit its crystallization. An extended annealing time is typically used to allow for crystallization. However, the presence of these soluble excipients can also cause melting of the frozen product during annealing. As such, Applicants discovered a balance between the amount of structure former, buffer salts, and cryo-lyoprotectant and the annealing conditions (i.e., temperature and time). In some embodiments, the amount of structure former in the virosome formulation can be about 1-20% w/w, about 3-15% w/w, about 4.5-10% w/w, about 4.5-8% w/w, about 5-10% w/w, about 6-10% w/w, about 7-9% w/w, or about 8% w/w. Applicants discovered that at values below 4.5% w/w of the structure former, some microstructural collapse may occur during freeze drying resulting in poor dispersion/disintegration of the freeze-dried dosage form. As such, a higher amount of the structure former was found to minimize or eliminate the microstructural collapse without drastically affecting virosome.

In addition, the base matrix formulation can also include a cryo-lyoprotectant. Examples of cryo-lyoprotectants include, but are not limited to, polyols such as trehalose, sugars such as sucrose, and amino acids such as lysine, oligosaccharides such as inulin (a medium chain oligosaccharide), or combinations thereof. A cryo-lyoprotectant can be used to protect the virosome from damage during subsequent freezing and freeze drying. However, the addition of a cryo-lyoprotectant can induce microstructural collapse of the dosage form matrix during freeze drying. As such, a balance should be struck to minimize microstructural collapse and at the same time preserving a sufficient number of virosomes to maintain the virosome quality for inducing an immune response. The amount of cryo-lyoprotectant in the base matrix formulation can be about 0.01-2% w/w, about 0.1-1.5% w/w, about 0.2-1% w/w, or about 0.25-0.75% w/w. As such, the net amount (hereinafter "(net)") of the cryo-lyoprotectant in the virosome formulation (i.e., liquid virosome concentrate plus base matrix formulation) can be about 0.5-6% w/w, about 0.5-5% w/w, about 0.5-4.5% w/w, about 1-4.5% w/w, about 1.5-4.5% w/w, about 1.5-3% w/w, about 1.5-2.5, about 2-3% w/w, about 2.5% w/w, or about 2% w/w.

Applicants discovered that at these levels, the cyro/lyoprotectant can provide sufficient cryo-lyoprotection without resulting in unacceptable microstructural collapse during freeze drying.

In some embodiments, the base matrix formulation can also include a muco-adhesive such as gum. Suitable gums include, but are not limited to, acacia, guar, agar, xanthan, gellan, carageenan, curdlan, konjac, locust bean, welan, gum tragacanth, gum arabic, gum karaya, gum ghatti, pectins, dextran, glucomannan, and alginates, or combinations thereof.

The base matrix formulation may also contain additional pharmaceutically acceptable agents or excipients. Such additional pharmaceutically acceptable agents or excipients include, without limitation, sugars, such as mannitol, dextrose, and lactose, inorganic salts, such as sodium chloride and aluminum silicates, gelatins of mammalian origin, fish gelatin, modified starches, preservatives, antioxidants, surfactants, viscosity enhancers, permeability enhancers, coloring agents, flavoring agents, pH modifiers, sweeteners, taste-masking agents, and combinations thereof. Suitable coloring agents can include red, black and yellow iron oxides and FD & C dyes such as FD & C Blue No. 2 and FD & C Red No. 40, and combinations thereof. Suitable flavoring agents can include mint, raspberry, licorice, orange, lemon, grapefruit, caramel, vanilla, cherry and grape flavors and combinations of these. Suitable pH modifiers can include citric acid, tartaric acid, phosphoric acid, hydrochloric acid, maleic acid, sodium hydroxide (e.g., 3% w/w sodium hydroxide solution), and combinations thereof. In some embodiments, the base matrix formulation and/or virosome formulation has an amount of a pH modifier to maintain a target pH of about 6-9, about 7-8, about 7.2-7.6, about 7.3-7.5, or about 7.4. Suitable sweeteners can include aspartame, acesulfame K and thaumatin, and combinations thereof. One of ordinary skill in the art can readily determine suitable amounts of these various additional excipients if desired.

The base matrix formulation can also include a solvent. In some embodiments, the solvent can be water (e.g., purified water). In some embodiments, the balance remaining of the base matrix formulation and/or virosome formulation is the solvent.

The base matrix formulation can be about 25-99% w/w, about 35-90% w/w, about 40-85% w/w, about 45-80% w/w, or about 50-75% w/w of the virosome formulation. In some embodiments, the base matrix formulation can be about 65-85% w/w, about 70-80% w/w, about 73-77% w/w, or about 75% w/w of the virosome formulation.

Making a Dosage Form Comprising the Virosome Formulation

Figure 2:
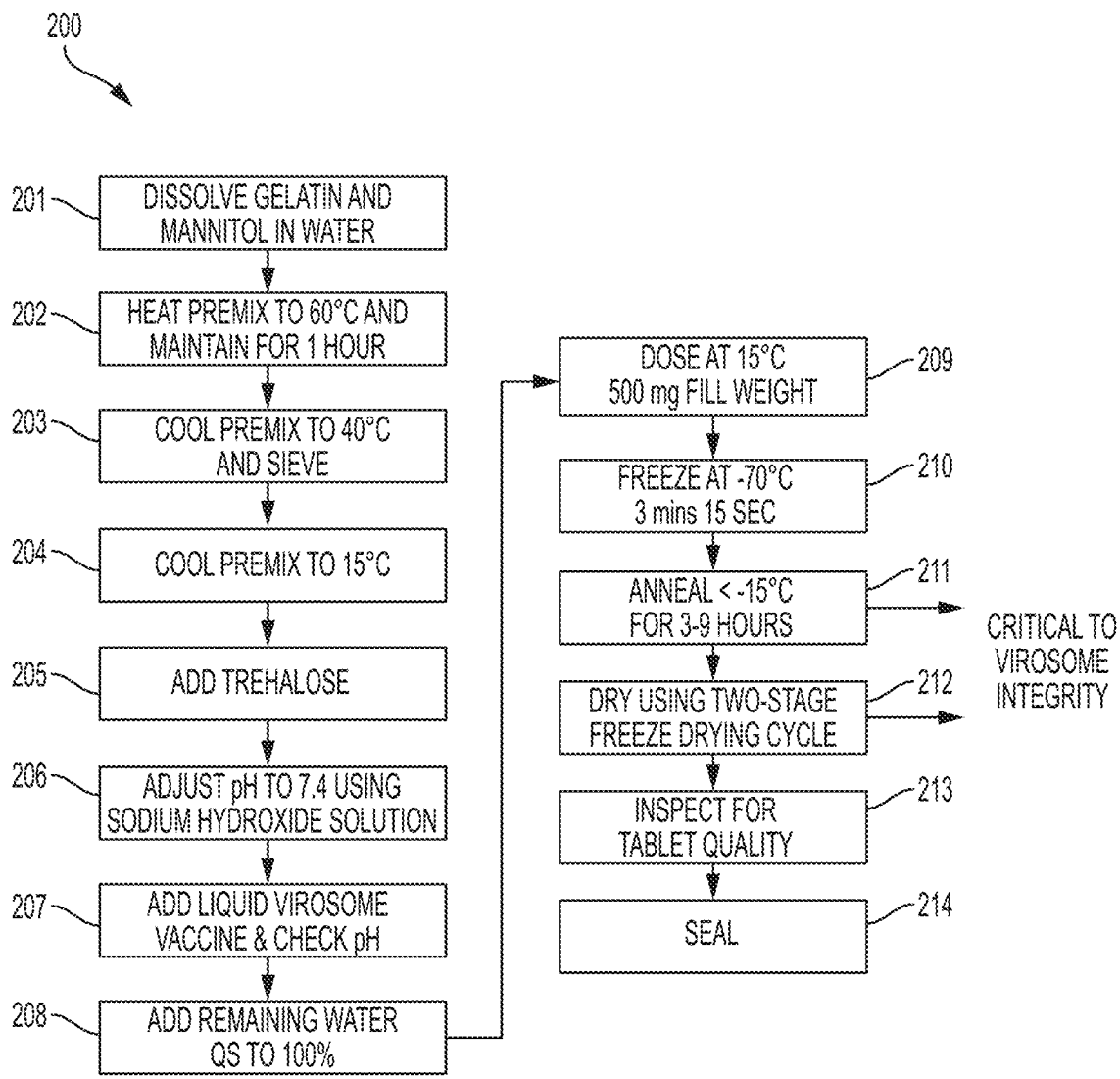
FIG. 2 illustrates a flowchart from matrix formulation to final sublingual tablets for producing a vaccine dosage form disclosed herein.

As stated above, a liquid virosome concentrate is mixed with a base matrix formulation to form a virosome formulation in step 101 suitable for the freeze-drying process. FIG. 2 provides a more detailed description of the process of forming a vaccine dosage form disclosed herein. In some embodiments, the base matrix formulation can be prepared by dissolving a matrix former and a structure former in a solvent to form a premix. For example, gelatin and mannitol can be dissolved in water as shown in step 201 of FIG. 2. The premix can be heated to about 40-80° C., about 50-70° C., about 55-65° C., or about 60° C. and maintained for about 45-75 minutes, about 55-65 minutes, or about 60 minutes. As shown in step 202, the premix can be heated to 60° C. and maintained for 1 hour. The premix can then be cooled to about 30-50° C., about 35-45° C., or about 40° C. and sieved before cooling down further to about 10-20° C.

or about 15° C. and maintained at this temperature throughout the rest of the process. As shown in step 203, the premix can be cooled to 40° C. and sieved. Next, the premix can be cooled to 15° C. as shown in step 204.

Next, the cryo-lyoprotectant can be added to the premix. For example, trehalose can be added to the premix as shown in step 205. Subsequently, the pH can be adjusted to about 6-9, about 7-8, about 7.2-7.6, about 7.3-7.5, or about 7.4 using a pH modifier. For example, the pH can be adjusted to 7.4 using a sodium hydroxide solution as shown in step 206. After the pH is adjusted, the liquid virosome concentrate can be added. After the liquid virosome concentrate is added, the pH can be rechecked (step 207) and, if necessary, adjusted to about 6.0-8.5, about 7-8, about 7.2-7.6, about 7.3-7.5, or about 7.4 using additional pH modifier. This mixture can be made up to a desired batch size with solvent (i.e., the virosome formulation). For example, an amount of water as necessary can be added to the mixture as shown in step 208.

At step 102 of FIG. 1, the liquid virosome formulation can be dosed into a preformed mold. As used herein, "dosed" refers to the deposition of a pre-determined aliquot of solution or suspension. As used herein, "preformed mold" refers to any suitable container or compartment into which an aqueous solution or suspension may be deposited and within which subsequently freeze dried. In certain embodiments of the present disclosure, the preformed mold is a blister pack with one or more blister pockets. Predetermined aliquots in an amount of about 150-1000 mg or about 500 mg wet filling dosing weight (also referred to as dosing fill weight) of the virosome formulation can be metered into preformed molds. In some embodiments, the virosome formulation can be dosed at about 10-20° C. or about 15° C. For example, the virosome formulation can be dosed at 15° C. with a 500 mg dosing fill weight as shown in step 209.

At step 103 of FIG. 1, the dosed virosome formulations can then be frozen in the preformed molds. The dosed virosome formulations in the preformed molds can be frozen by any means known in the art. For example, the formulations can be passed through a cryogenic chamber (e.g., liquid nitrogen tunnel). The temperature during freezing can be between about −50 to −100° C., about −60 to −90° C., about −60 to −80° C., about −65 to −75° C., or about −70° C. The freezing duration can range from about 1.5-5 minutes, about 2-4.5 minutes, about 2.5-4 minutes, about 3-4 minutes, about 3-3.5 minutes, or about 3.25 minutes. For example, the dosed virosome formulation can be frozen at −70° C. for 3 mins and 15 seconds as shown in step 210.

At step 104 of FIG. 1, the frozen units in the preformed molds can be collected and placed in a freezer at a temperature of less than about −25° C., about −20° C., about −15° C., about −10° C., about −5° C. and annealed (i.e., frozen hold) for a period of time to crystallize the structure former. Structure former crystallization can provide the frozen units with the structural strength to prevent the collapse of the frozen units during freeze drying. This can be critical to the virosome integrity. The annealing time can range from about 3-9 hours, about 4-8 hours, about 5-7 hours, or about 6 hours. For example, the frozen units can be annealed at less than −15° C. for about 3-9 hours as shown in step 211.

After annealing, the annealed frozen units can be freeze-dried in step 105 to form the dosage form. During the freeze-drying process, the water is sublimated from the frozen units. In some embodiments, the frozen units can be loaded onto the shelves of a freeze-drier. In some embodiments, the freeze-drier can be precooled to about −15 to −35° C., about −20 to −30° C., or about −25° C. Once the annealed frozen units are in the freeze-drier, the freeze-drying cycle can be initiated. In some embodiments, a vacuum can be pulled and the shelf temperature raised once the freeze-drying cycle is initiated. The freeze-drier can operate at low pressure (i.e., vacuum). In some embodiments, the freeze-drier can operate at a pressure of about less than or equal to 1000 mbar, about 900 mbar, about 800 mbar, about 700 mbar, about 600 mbar, about 500 mbar, or about 400 mbar.

Applicants discovered a two-step freeze-drying cycle (step 212) that can achieve structural robustness of the dosage form as well as minimally damaging the virosome in the dosage form. The two-step freeze-drying cycle can include a first step of holding the frozen units at about −5° C. to −25° C., about −10° C. to −20° C., about −13° C. to −17° C., or about −15° C. for about 12-36 hours, about 18-30 hours, about 20-28 hours, or about 24 hours. In addition, the two-step freeze-drying cycle can include a second step that follows the first step. The second step can include holding the frozen units at about 0° C. to −20° C., about −5° C. to about −15° C., about −8° C. to about −12° C., or about −10° C. for about 6-30 hours, about 12-24 hours, about 14-22 hours, or about 18 hours. At the end of the two-step freeze drying cycle, the temperature of the freeze-drier can be raised to about ambient temperature (i.e., about 20-25° C. or about 23° C.

In some embodiments, the two-stage freeze-drying process can include pre-cooling to the freeze-drier to about −25° C., ramping the freeze-drier for 2 hours to −15° C., holding the freeze-drier at −15° C. for 24 hours, ramping the freeze-drier to −10° C. for 2 hours, holding at −10° C. for 18 hours, ramping to 0° C. for 15 mins, and ramping to 23° C. for 15 mins in that order.

The freeze-dried dosage forms can be removed from the freeze-drier and inspected for any defects (quality inspection as described below) at step 213. The dosage forms can then be placed in a storage cabinet at atmospheric humidity less than about 35% RH before the dosage forms can be sealed in their preformed molds. The sealing process (step 214) can place a lidding foil on the preformed molds and provide blisters of freeze-dried dosage forms.

The water in the freeze-dried dosage forms can be removed via sublimation during freeze-drying. Accordingly, the remainder of the virosome concentrate in the freeze-dried dosage form excluding the cryo-lyoprotectants (i.e., the virosomes, antigens, adjuvants, and buffer system remaining from the freeze-dried virosome concentrate) can be about 1-5 wt. %, about 2-4 wt. %, about 2.5-3.5 wt. %, about 2.6-3.4 wt. %, about 2.7-3.3 wt. %, about 2.8-3.2 wt. %, about 2.9-3.1 wt. %, or about 3-3.1 wt. % of the dosage form.

As stated above, the target molecule(s) is included in the dosage forms disclosed herein in an amount, which is sufficient to render it immunogenic when provided in a dosage form. A person of skill in the art can readily determine the immunogenic amount for a given disease or infection based on, among other facts, route of administration, age and weight of the patient to whom the dosage form will be administered. In some embodiments, the solid dosage form can contain from 0.01-250 µg of each target molecule (e.g., HIV-1 P1 peptide and/or rgp41).

In some embodiments, at least one of the cryo-lyoprotectants in the freeze-dried dosage form can be about 5-20 wt. %, about 8-18 wt. %, about 10-15 wt. %, about 11-15 wt. %, or about 12-15 wt. % of the dosage form. In some embodiments, at least one of the cryo-lyoprotectants in the freeze-dried dosage form can be about 1-5 wt. %, about 1-4 wt. %, or about 2-4 wt. % of the dosage form.

In some embodiments, the amount of matrix former in the dosage form can be about 20-50 wt. %, about 25-45 wt. %, about 25-40 wt. %, about 30-40 wt. %, about 33-37 wt. %, or about 35-37 wt. %. In some embodiments, the amount of structure former in the dosage form can be about 27-65 wt. %, about 27-60 wt. %, about 40-55 wt. %, or about 45-50 wt. %. In some embodiments, the remainder of the pH modifier in the freeze-dried dosage (e.g., sodium hydroxide) can be about 0.01-0.08 wt. %.

aliquot of 500 mg (dosing fill weight) of the aqueous virosome formulation was metered into pockets preformed blister, followed by freezing and freeze drying. Dosing fill weights may range from 150 mg to 1000 mg and the compositions of the HIV-1 liquid virosome concentrate can be adjusted to meet the target dose required. Please note that the following target ranges can be dependent on the purpose and the further use, e.g., for animal studies or for human studies. Thus, the other target concentrations may be useful for other purposes.

TABLE 1

| Example of Lipid based Particle Concentrates for a 500 mg dosing fill weight Zydis ® virosome formulation | Example Target Molecules and Excipients In Lipid based Particle Concentrates |
| --- | --- |
| HIV vaccine MYM-V202 (4x concentrate for 25% loading of liquid virosome in the Zydis ® virosome formulation | Target molecule (P1 antigen): 50-450 µg/mL<br>Target molecule (rgp41 antigen): 50-400 µg/mL<br>HA excipient: 10-160 µg/mL<br>Adjuvant (e.g. 3 M-052): 8-140 µg/ml<br>Phospholipids: 0.5 to 5 mg/mL<br>Sodium Chloride: 50-150 mM<br>HEPES 10-50 mM<br>Trehalose: 4-10% w/w<br>pH 6.5 to 8.0 |
| HIV vaccine MYM-V202 (2x concentrate for 50% loading of liquid virosome in the Zydis ® virosome formulation) | Target molecule (P1 antigen): 25-225 µg/mL<br>Target molecule (rgp41 antigen): 25-200 µg/mL<br>HA excipient: 5-80 µg/mL<br>Adjuvant (e.g. 3 M-052): 4-70 µg/ml<br>Phospholipids: 0.5 to 5 mg/mL<br>Sodium Chloride: 50-150 mM<br>HEPES 10-50 mM<br>Trehalose: 2-5% w/w<br>pH 6.5 to 8.0 |
| Placebo vaccine VP02 (4x concentrate for 25% loading of liquid virosome in final Zydis ® virosome formulation) | HA excipient: 10-160 µg/mL<br>Adjuvant (e.g. 3 M-052): 8-140 µg/ml<br>Phospholipids: 0.5 to 5 mg/mL<br>Sodium Chloride: 50-150 mM<br>HEPES 10-50 mM<br>Trehalose: 4-10% w/w<br>pH 6.5 to 8.0 |

The dosage forms of the present disclosure are dissolving dosage forms and accordingly have the distinct advantage of a faster disintegrating time. The route of administration may be oral, vaginal or nasal, though preferably oral (i.e., sublingual and/or buccal). Once placed in the oral cavity and in contact with saliva, a dosage form can disintegrate within about 1 to about 180 seconds, about 1 to about 120 seconds, about 1 to about 60 seconds, preferably within about 1 to about 30 seconds, more preferably within about 1 to about 10 seconds and most preferably in less than about 5 seconds.

Formulations, Test Methods, and Examples

For the examples, a liquid virosome concentrate prepared from influenza virus was used. The virosomes contained the influenza HA as well as added antigens and adjuvants. Two virosome preparations were made, each containing a single antigen derived from the HIV envelope glycoprotein. The liquid virosome concentrate was a mixture of two virosome preparations. The two HIV-gp41 derived antigens were the P1 peptide representing the last 35 C-terminal ectodomain residues and the truncated rgp41 devoid of cluster I and the last 21 C-terminal ectodomain residue. Adjuvant 3M-052 was either present or absent in either virosome preparation. The virosomes were suspended in HEPES-Sodium Chloride buffer containing 142.5 mM sodium chloride and 50 mM HEPES at pH 7.4. In addition, trehalose (a cryo-lyoprotectant) was tested in the range of 0-10% w/w of the liquid virosome concentrate. The following Table 1 summarizes the target compositions of the HIV-1 liquid virosome concentrate used for some of our experiments, during which an In some of our experiments, the target dose for HA and the HIV-1 antigens for each tablet were 20 µg HA, 25 µg P1, and 50 µg rgp41. To achieve these doses, a high payload of the liquid virosome concentrates in combination with high wet filling dose weight were required. Table 2 shows the various combinations of liquid virosome concentrate loading (ranging from 25-50% w/w) with wet fill dosing weight (ranging from 250 to 1000 mg). The wet fill dosing wet is the amount of aliquot of the virosome formulation metered per dose prior to freeze-drying.

TABLE 2

| Liquid virosome concentrate HA and antigen content | Liquid virosome concentrate % loading in base matrix formulation | Virosome vaccine Target dose Dosing fill per tablet weight HA/P1/rpg41 | |
| --- | --- | --- | --- |
| HA 80 µg/ml (with adjuvant 3 M -052) P1 100 µl/ml rgp41 200 µg/ml | 25% w/w<br>50% w/w | 1000 mg<br>500 mg | 20 µg/25 µg/50 µg<br>20 µg/25 µg/50 µg |
| HA 160 µg/ml (with adjuvant 3 M -052) P1 200 µl/ml rgp41 400 µg/ml | 25% w/w<br>50% w/w | 500 mg<br>250 mg | 20 µg/25 µg/50 µg<br>20 µg/25 µg/50 µg |

A 25% loading of the liquid virosome concentrate can be added to the base matrix formulation. The dosing filling dose weight can be 500 mg. Table 3 shows the range of HA and antigen contents evaluated.

TABLE 3

| Component | Target composition in Liquid concentrate | Composition Supplied for evaluation | Composition in a 25% loading formulation |
|---|---|---|---|
| Virosome tagged with antigens and adjuvants | HA: 10-160 µg/ml<br>P1: 50-450 µg/ml<br>rgp41: 50-400 µg/ml<br>3 M-052: 8-140 µg/ml | HA: 70-160 µg/ml<br>P1: 40-100 µg/ml<br>rgp41: 70-230 µg/ml<br>3 M-052: 16-65 µg/ml | HA: 18-40 µg/ml<br>P1: 10-25 µg/ml<br>rgp41: 17.5-57.5 µg/ml<br>3 M-052: 4-16.3 µg/ml |
| Sodium Chloride | 50-150 mM | 142.5 mM | 35.625 mM |
| HEPES | 10-50 mM | 50 mM | 12.5 mM |
| Trehalose | 4-10% w/w | 3.5-7% w/w | 0.9-1.75% w/w |

The presence of buffer in the aqueous composition can depress the freezing point, thus making it difficult to freeze the formulation composition and maintain its frozen state. In addition, collapse of the tablet matrix structure can also occur during the freeze-drying as buffer salts can depress the crystallization of mannitol during the anneal process. Crystallization of mannitol is required to provide strength and structure to the tablet matrix to prevent structure collapse. However, crystallization of mannitol can damage the virosome particles during freezing, annealing, and freeze-drying. A lower percentage loading of the liquid virosome concentrate (e.g. 25% loading) lands to reducing this impact. A combination of lower percentage loading of the liquid virosome concentrate and a larger dosing fill weight can also be considered.

A high wet fill dosing weight of the virosome formulation in combination with a formulation composition with high buffer content can also make it more difficult to freeze and maintain the structure to minimize collapse during freeze-drying. However larger tablets (e.g. 1000 mg dosing fill weight) can cover bigger surfaces area and can potentially improve virosome passage. When a high wet fill dosing weight is required, formulation composition with low buffer content is preferred.

Table 4 (Formulation 1) summarizes the aqueous compositions of the virosome formulation and the corresponding composition for the tablet virosome evaluated herein. The following formulations and tablets were made according to the steps shown and described in FIG. 2. In addition, the frozen formulations were subjected to the two-step freeze-drying process with a vacuum of 500 mbar of: (a) −25° C. pre-cool; (b) Ramp for 2 hours to −15° C.; (c) Hold @ −15° C. for 24 hours; (d) Ramp to −10° C. for 2 hours; (e) Hold @ −10° C. for 18 hours; (f) Ramp for 15 mins to 0° C.; (g) Ramp for 15 mins to 23° C. Next, the vacuum was released and the freeze drier returned to atmospheric pressure.

The concentration of each ingredient (% w/w) is the amount prior to removal of the water present in the liquid virosome concentrate, sodium hydroxide solution, and the water used for preparing by sublimation during lyophilization. Also, the following table includes amounts which each ingredient may be ranged.

TABLE 4

| Ingredient | % w/w range evaluated | % w/w Formulation 1/2 | Amount in mg for a 500 mg wet dosing fill weight | Amount in mg in post freeze drying |
|---|---|---|---|---|
| Liquid Virosome concentrate | 25-50% | 25% | 125 mg | ~2.5-2.6 mg* |
| Trehalose | 0.5%-4.5% | 2%** (net) | 10 mg | 10 mg** (net) |
| Fish Gelatin | 4-6% | 6% | 30 mg | 30 mg |
| Mannitol | 4.5-8% | 4.5%/8% | 40 mg | 40 mg |
| Sodium Hydroxide Solution (e.g. 3% w/w) | qs pH 7.4 | qs pH 7.4 | ~1.3 mg (qs pH 7.4) | ~0.04 mg (water removed by sublimation) |
| Water (for preparing the aqueous matrix mixture) | qs 100% | qs 100% | ~293.7 mg | Water removed |
| Total weight of freeze dried vaccine tablet | N/A | N/A | N/A | ~82.64 mg |

*As stated above, the liquid virosome concentrate included virosomes suspended in a buffer system of 142.5 mM NaCl and 50 mM HEPES with 5% w/w trehalose. For a 25% loading of the virosome formulation in a 500 mg dosing fill weight (i.e., 125 mg of the liquid virosome concentrate), the estimate dry matter with water sublimated of the virosomes, antigens, adjuvants, NaCl, and HEPES (excluding trehalose) is about 2.5-2.6 mg.
**This is the net amount of trehalose in the virosome formulation and the dosage form. As such, this amount includes trehalose from the liquid virosome concentrate as well as trehalose added from the base matrix formulation.

Properties of Freeze-Dried Dosage Forms:

The freeze-dried dosage forms can be stable in physical attributes and virosome quality (particle size characteristics and antigen content) and can be stored independent of cold chain storage conditions. In addition, the freeze-dried dosage forms can allow the virosomes to be resistant to accidental exposure to sub-zero storage conditions during storage or transportation.

Dosage Form Physical Characteristics:

Freeze dried tablets with acceptable physical characteristics were produced. The physical attributes of the tablets include appearance, dispersion characteristics, disintegration times, and moisture content.

Tablet Appearance of ten freeze-dried tablets are tested. Each tablet is removed from the blister package. A visual inspection on each tablet for surface defect on the tablet surface and base is performed. The criterion is that the freeze-dried tablet should have good appearance with no surface defects. In addition, the tablets should be of sufficient robustness for their removability from the blister pocket without breakage.

Dispersion Characteristics (in-vitro test): A minimum of 5 tablets are tested. First, a beaker is prepared containing approximately 200 mL of purified water at 20° C.±0.5° C. Each tablet is then removed from the blister package and the tablet is placed base down on the surface of the water. The time is taken for the time each tablet takes to fully wet or dissociate. Wetting the time taken for the unit to fully wet. The wetting of the tablet can occur in patches, eventually merging together so that the whole unit is wet. The dispersion test is considered complete when the center of the unit is a wetted mass. Thus, the wetting time is taken from when the center of the unit has wetted through as this is the thickest part of the unit. The wetting time is recorded for each of the five tablets. The maximum time for each test is 60 seconds. Time longer than this may be written simply as greater than 60 seconds. Dissociation=the time taken for the unit to break apart. This time can be taken when the unit starts to fall apart at the edges. The dissociation time is recorded for each of the five tablets. The maximum time for each test is 60 seconds. Times longer than this may be written as greater than 60 seconds. Occasionally, the unit will not fully wet or dissociate completely inside of this time limit. At times, the unit may have hard lumps in it; other times it may have not wetted on the surface at all. In addition, the whole unit may be covered in a hard skin. A note of this is made in the description if it happens, citing "hard lumps", or "skin remains", as appropriate. The formation of "hard lumps" and/or "skin" can be an indication of microstructural collapse during freeze-drying. FIGS. 3A-C show a simplified representation of the three possible non-dispersed states, with a side view and a top view of the units as they would appear in the water. The photos in FIGS. 3A-C show some representative units for the same categories. The criterion for the dispersion characteristic test is if the 5 tablets can be fully wetted and/or dissociated into a palpable mass without the presence of hard lumps and skin in 60 seconds or less. In some embodiments, the dosage forms disclosed herein can be fully wetted and/or dissociated into a palpable mass without the presence of hard lumps and/or skin in 60 seconds or less.

Disintegration Time (in-vitro test): Six tablets are used for this test. Six beakers are filled with purified water and placed in a water bath controlled at 37° C.±0.5° C. Each tablet is then removed from the blister package. Carefully place a wire clip onto each of the six tablets. Ensure that the clip grips the tablet without causing damage. Next, perform the test as described in the Pharmacopeia. An example of such a test is the United State Pharmacopeia (701) Disintegration. The maximum disintegration time is recorded for each tablet. The criterion for the disintegration time test is that the disintegration time should not be more than 60 seconds for each of the six tablets. In some embodiments, the dosage forms disclosed herein can have a disintegration time of less than 60 seconds.

Moisture Content: A Methron 831 Karl Fischer Coulometer with a 744 Oven Sample Processor (Metrohm, Herisau, Switzerland) is used to determine the water content of the tablet. A tablet is accurately weighed and placed it in a glass vial. The vial is crimp shut immediately to ensure no moisture ingress. Then the sample vial is placed in the 744 Oven Sample Processor and set the temperature to 102° C. The evaporated moisture is titrated using a Hydranal Coulometric AG Oven reagent to quantify the amount of water released. The test is performed in triplicate and the mean is recorded. The criterion for the moisture content is if the freeze-dried dosage form has a moisture content of less than about 8%, preferably less than 6%, and more preferably less than 4%. In some embodiments, the dosage forms disclosed herein can have a moisture content of less than about 8%, preferably less than 6%, and more preferably less than 4%.

Virosome Characteristics:

The freeze-dried dosage forms that contain the virosomes can be sufficiently preserved in terms of proportion of intact virosomes from the starting liquid virosome population, its particle size and surface antigens content required for the immunogenicity and immunological benefits of the virosomes. The virosome structure can be destroyed by the freeze-drying process used for producing the dosage forms. As such, virosome particulate characteristics are assessed from a solution of a reconstituted freeze-dried tablet. The virosomes can exist as intact individual particles and as clusters of different sizes, all being immunogenic but having different antigen/epitope exposure, and harboring different ability to cross the sublingual barrier. The virosomes may be characterized in terms of (a) mean particle size and (b) proportion of virosome preservation (intact virosomes).

Virosome Particle Size and Particle Concentration (counts of virosome particles per mL) assessment using NTA technique: Nanoparticle Tracking Analysis (NTA; with NanoSight NS300 instrument) is a sensitive method that can identify different particle sizes in the range of 30-1000 nm present in a solution. Particles in a sample solution can individually be tracked and simultaneously analyzed by direct observation. Nanoparticles move under Brownian movement due to the random movement of water molecules surrounding them. Small particles move faster than larger particles. Brownian motion of each particle is followed in real-time via video and the NTA analyzes the Brownian motion to determine the particle size. The diffusion coefficient can be calculated by tracking the movement of each particle and then through the application of the Stokes-Einstein equation, the particle size can be calculated. This particle-by-particle methodology produces high resolution results for particle size distribution and concentration (i.e., number of particles in a known volume of liquid). The target values for optimum detection for the instrument detection are summarized in the following Table 5.

TABLE 5

| Quality Indicator | Target | Rationale |
| --- | --- | --- |
| PPF (Particles Per Frame) | 50-100 | Particle count affects resolution achievable and statistical accuracy of profiles generated |
| Number of Valid Tracks | >5000 | Statistical accuracy of profiles generated for poly-disperse samples |
| S:N (Signal to Noise ratio) | High | Improved detection of small or faint particles |
| SD (Standard Deviation) | Low | Less variable data gives higher confidence in results |

TABLE 5-continued

| Quality Indicator | Target | Rationale |
| --- | --- | --- |
| Appearance of profile | Good: non-Gaussian, minimal shouldering on peaks | Less noise present in data, clear particle size populations |

The test sample must be in liquid form. For this work, the virosome vaccine is supplied in liquid form. For test samples from the vaccine formulations disclosed herein, the mix is supplied in liquid form, a frozen unit is thawed to liquid form before testing, and a freeze-dried dosage form is reconstituted with water buffer to liquid form. The test sample should not be too concentrated. A liquid test sample can be diluted further with HN buffer as appropriate to optimize the detection. The dilution buffer can be of high purity, and can be filtered at least through a 0.22 μm filter prior to use. The experimental parameters set for NTA analysis are summarized in the following Table 6.

TABLE 6

| Parameter | Setting |
| --- | --- |
| Sample Dilution | Dependent on content (can range from 1:100 to 1:8000 depending on the concentration of virosome counts in the diluted test samples) |
| Number of Captures | 5 |
| Capture Duration | 60 seconds |
| Temperature control | 25° C. |
| Viscosity | 0.9 Cp |

The samples were measured by NTA as known in the art. In some embodiments, the virosome particle range including fragments and clusters disclosed herein can be from about 50-500 nm. In some embodiments the virosomes particles that are intact virosomes can be in the range of about 70-400 nm or about 70-200 nm (main peak). In some embodiments, the mean diameter of the virosome particles can be about 70-200 nm, about 100-175 nm, about 125-155 nm. For detection purpose, the particle concentration of virosome population in the sample can be at least $10^{10}$ counts/mL.

Proportions of Virosome Preservation Assessment Using Flow Cytometry: Flow cytometry is used for this assessment. First, the starting liquid virosome particles is labelled (reference sample representing 100% of the starting material) by inserting a lipophilic dye DiI (long-chain dialylcarbocyanin) into the lipid bilayer of the virosomes. (Labelling with DiI has no measurable effect on the particle size). Secondly, the freeze-dried tablet is reconstituted and labeled the virosomes in the freeze-dried tablet with DiI (the test sample). Then the samples are analyzed using AMNIS imaging flow cytometer and the events between the reference (liquid virosomes before freeze-drying) and the test samples (freeze-dried virosomes) are compared to estimate the proportions of virosome preservation following freeze drying in terms of: (a) percentage of virosome recovery and (b) percentage of virosome clusters. In some embodiments, the percentage of recovery of the virosome as single particles can be about 20-50%, about 30-50%, or about 40-50% of the starting material. In some embodiments, the percentage of virosome clusters (doublets, triplets or higher number forms) can be about less than 50%, about 25%, about 10%, or about 5%.

Content of Virosome Hemagglutinin (HA), HIV-1 Antigen P1, HIV-1 Antigens and Adjuvant The influenza HA, HIV-1 antigens, and adjuvant contents of the virosome can be quantified by various methods. These are tabulated in Table 7 below.

TABLE 7

| Content to be quantified | Methods |
| --- | --- |
| Influenza HA | Immunoblot assay |
|  | SRID assay |
|  | ELISA |
|  | HPLC assay |
| HIV-1 antigens | Immunoblot assay |
|  | HPLC assay |
|  | ELISA |
| Adjuvant | UV spectroscopy assay |
|  | HPLC assay |

Immunoblot Assay Method for HA, P1, and rgp41: In this analysis, the formulation (liquid virosome concentrates or reconstituted freeze-dried dosage forms containing the virosomes) can be absorbed onto nitrocellulose membrane and the antigens are maintained in their native state due to the absence of heating procedure, denaturing or reducing agents. This assay detects all antigens accessible to the specific antibodies and is indicative for major antigen degradation or denaturation that destroys or blocks access to the specific epitope. It also indicates if specific excipients could prevent antibody binding to its antigen. To prepare the freeze-dried dosage forms for analysis (test samples), each tablet is dissolved in 0.5 mL of water (i.e., reconstitute the freeze-dried tablet back to the composition of virosome formulation prior to freeze-drying). To prepare a positive control, a sample of liquid virosome concentrate is diluted with ultrapure water (the dilution is 4 folds). The liquid virosome concentrate ideally is the same batch that is used in making the dosage form test sample. Serial 2-fold dilutions of all the test samples and the positive control are prepared. Additional positive controls like purified HA and rgp41, and synthetic P1 may be used as well. A 1.5 μL of each sample and the positive control is spotted onto the dry nitrocellulose membrane (with increasing dilution from left to right—undiluted, ½, ¼, ⅛, 1/16, 1/32, 1/64, 1/128). The dry membrane is blocked with 1% (w/v) casein and incubate with specific antibody solution—the human monoclonal antibody (mab) 2F5 specific for HIV-1 P1 antigen and the rabbit anti-rgp41 serum for HIV-1 rgp41 antigen. After incubation, the nitrocellulose membrane is washed. Then, the bound specific antibodies with fluorescent labelled secondary antibodies (anti-human or anti-rabbit) are detected using a far-red fluorescence scanner that allows simultaneous detection of 2 different fluorescent labels at 700 nm and 800 nm. The fluorescence raw data signal for each sample spot (from lowest to highest) is compared to the respective dilution of the positive control spot (in % of the positive control). An arithmetic average of the sample percentage is calculated.

UV Spectroscopy Assay for 3M-052: The adjuvant molecule 3M-052 has several UV adsorption peaks. Some of these peaks overlap with the absorption of lipids and proteins. Determination was done by UV spectroscopy at 320 nm.

HPLC Assay for P1 and rgp41: The HIV antigens P1 and rgp41 were separated by reversed phase high pressure liquid chromatography on a C18 column using a water to acetonitrile gradient. Determination was done by UV spectroscopy at 280 nm, and peak areas were quantified by the HPLC system software.

ELISA endpoint antibody titer: Maxisorp 96-well plate (Nunc-flat bottom) and Polysorp plates were respectively coated at 4° C. for 16 hours with 0.1 mL of rgp41 or P1 peptide (2 µg/mL) prepared in PBS pH 7.4. Plates were washed 3 times with PBS with 0.05% v/v) TWEEN® 20 (PBST), then the blocking solution 1% BSA prepared in PBST was added to each well and incubated 2 hours at room temperature (RT). Plates were washed three times with PBST prior adding 0.1 mL per well of pre-immune serum diluted at 1/1000 or immune serum serial dilutions (from 1/1000 to 1/64,000) prepared in 0.1% BSA in PBST and incubated for 2 hours at RT. Plates were washed three times with PBST and incubated for 2 hours at RT with the goat anti-rat IgG-HRP diluted 1:4000 in 0.1% BSA in PBST. Plates were washed again before adding 0.1 mL of the colorimetric substrate o-phenylenediamine (OPD) and the reaction was stopped with 2M H2SO4, followed by plate reading at 492 nm.

frozen products were collected and placed in a freezer at a temperature of <−15° C. and annealed for 6 hours frozen hold before lyophilisation. A 2-step FD cycle using −15° C. for 24 hours followed by −10° C. for 18 hours was then used. The blisters of freeze-dried tablets were sealed in sachets and stored at ambient condition.

The physical characterisation of the lyophilised tablets (appearance and dispersion time) were assessed according to the tests explained above. In addition, the virosome particle size in the lyophilised tablets were characterised according to the tests explained above. The results are summarised in Table 8 below.

TABLE 8

| Mannitol 4.5% (Formulation 1) | Mannitol 8% (Formulation 2) |
|---|---|
| Appearance: Good (n = 182) | Appearance: Good (n = 184) |
| Dispersion Time (n = 8) | Dispersion Time (n = 8) |
| Wetting: >60 s (2 units-skin, 5 units-hard lumps) | Wetting: <28 s |
| Dissociation: >60 s (didn't fully dispersed) | Dissociation: <36 s |
| NTA Analysis | NTA Analysis |
| Freeze dried tablet: 136 nm (main peak) | Freeze dried tablet: 140 nm (main peak) |
| % virosome particle (<200 nm): >50% | % virosome particle (<200 nm): >50% |

Example 1: Use of High Mannitol Level (8% w/w) in Conjunction with Low Temperature Freeze Drying Cycle to Reduce Microstructural Collapse During Freeze Drying without Damaging the Virosome Integrity Mannitol is used in dosage forms to increase structural robustness. Due to the presence of high levels of buffers and the addition of trehalose to protect the virosome particles, the use of mannitol at typical level of 4.5% w/w was unable to provide sufficient structural support during freeze drying. Thus, microstructural collapse occurred.

However, Applicants discovered that by using a combination of higher level of mannitol and low temperature freeze drying cycles, a structurally more robust freeze-dried tablet can be achieved. This example shows data comparing a formulation containing 4.5% w/w mannitol with that containing 8% w/w mannitol. In both formulations, a 25% w/w loading of liquid virosome concentrates MYM-201 lot 160125-1 supplied by Mymetics containing HA 70-80 µg/ml, P1 40-50 µg/ml, rgp41 70-80 µg/ml (A/Brisbane/59/2007 (H1N1) in HN buffer pH 7.4 (50 mM HEPES, 142.5 mM NaCl) was used in the virosome formulation. The fish gelatine and net trehalose levels were kept at 6% w/w and 2% w/w of the virosome formulation, respectively. As illustrated in FIG. 2, the formulations were dosed with a 500 mg dosing fill weight aliquot at 15° C. into blister pockets of aluminum trays. The trays containing the dosed aqueous vaccine mix were frozen by passing the aluminium trays through a freezing chamber set at −70° C. for a duration of 3 minutes 15 seconds. The aluminium trays containing the All the tablets had good appearance. The 4.5% w/w mannitol formulation has poor dispersion behaviour with skin and/or hard lumps seen in the tablets due to microstructural collapse. Increasing the formulation to 8% w/w which promotes the crystallisation of mannitol improved structure of the freeze-dried tablet. The formulation with 8% w/w mannitol has a good dispersion behaviour and gave a soft and palpable mass. In combination with low temperature freeze drying cycle, the virosome particle in the freeze-dried tablet was not affected. The virosome particle size in the freeze-dried tablets was comparable overall between the formulations.

Example 2: Stability Data of Freeze-Dried Vaccine Dosage Forms (Formulation 1) Stored for 3 Months Under ICH Conditions The liquid virosome concentrates is generally stable at 2-8° C. but the liquid HIV virosomal vaccine has a limited shelf life of few months due to important chemical modifications taking place on the antigens, while there is no aggregation. With solid vaccine form with low moisture content, such modifications are expected to be slowed down and minimal overtime, extending the shelf life >1 year. The stability of the virosome vaccine in the form of a freeze-dried tablet Formulation 1 is illustrated in this example. Liquid virosome concentrate batch MYM V202 lot 170130-1 supplied by Mymetics comprising of approximately 100 µg/ml HIV-1 P1, 230 µg/ml HIV-1 rgp41, 130 µg/ml HA (A/Brisbane/59/2007 (H1N1), 65 µg/ml adjuvant 3M-052 in HN buffer pH 7.4 (50 mM HEPES, 142.5 mM NaCl) with 7% w/w trehalose was supplied for the manufacture of lyophilized vaccine tablets (batch Z33787A101).

To prepare the vaccine tablet, a liquid virosome formulation mix was prepared first. It contained 25% w/w of liquid virosome concentrate batch MYM V202 lot 170130-1, 6% w/w fish gelatin, 4.5% w/w mannitol, 2% w/w (net) trehalose, sodium hydroxide solution (quantum satis) to pH 7.4, and purified water (quantum satis) to 100% w/w.

The liquid virosome formulation mixture was dosed with a 500 mg dosing fill weight aliquot at 15° C. into blister pockets of aluminum trays. The trays containing the dosed aqueous vaccine mix were frozen by passing the trays through a freezing chamber set at −70° C. for a duration of 3 minutes 15 seconds. The aluminium trays containing the frozen products were collected and placed in a freezer at a temperature of <−15° C. A 2-step FD cycle using −15° C. for 24 hours followed by −10° C. for 18 hours was then used.

The blisters of freeze-dried tablets were sealed in sachets and placed on storage for 3 months at 5° C., 25° C./60% relative humidity, and 40° C./75 relative humidity. The results at initial testing and at 3 months testing are summarized in Table 9 below.

TABLE 9

| Test | Initial | 5° C./ 3 month | 25° C. @ 60% RH/ 3 month | 40° C. @ 75% RH/ 3 month |
|---|---|---|---|---|
| Appearance | Good | Good | Good | Good |
| Moisture Content (% w/w) | 5.22 | 5.20 | 5.76 | 4.83 |
| Disintegration Time (sec) | <13 | <23 | <41 | <25 |
| NTA: Main Peak (nm) | 101 | 120 | 124 | 124 |
| NTA: % virosome particle (<200 nm): | >50% | >50% | >50% | >50% |

The stability data shows that the tablet appearance was good and consistent between batches. The moisture content was 5-6% w/w with little difference between the different stability conditions over the 3-month storage period. As this formulation contains 4.5% w/w mannitol, there is some microstructural collapse during freeze drying as indicated in the variability in disintegration time. In terms of virosome particle size, the DLS and NTA data showed no discernible difference in the virosome particle size between tablets stored at the various stability conditions. The starting liquid virosome concentrates has >50% of the particle <200 nm. The results show that virosome <200 nm from the reconstituted unit is essentially preserved to the similar order of magnitude.

Figure 4:
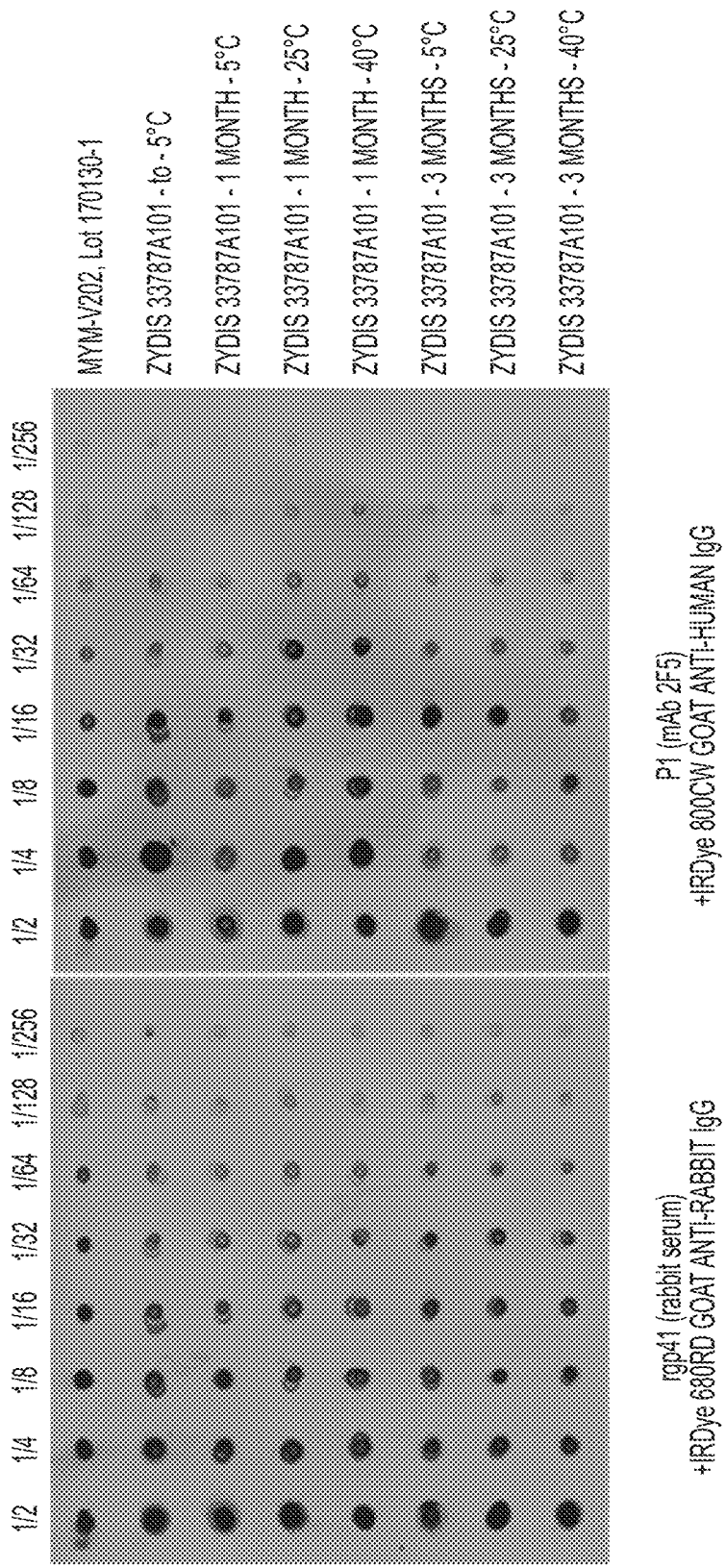
FIG. 4 is a photo of immunoblots showing anti-P1 and anti-rgp41 specific antibody binding to virosomes-P1 and virosomes-rgp41 from reconstituted Zydis® sublingual tablets stored at 5° C., 25° C., and 40° C. over 1 and 3 months (analysis of Example 2 disclosed herein).
Figure 5:
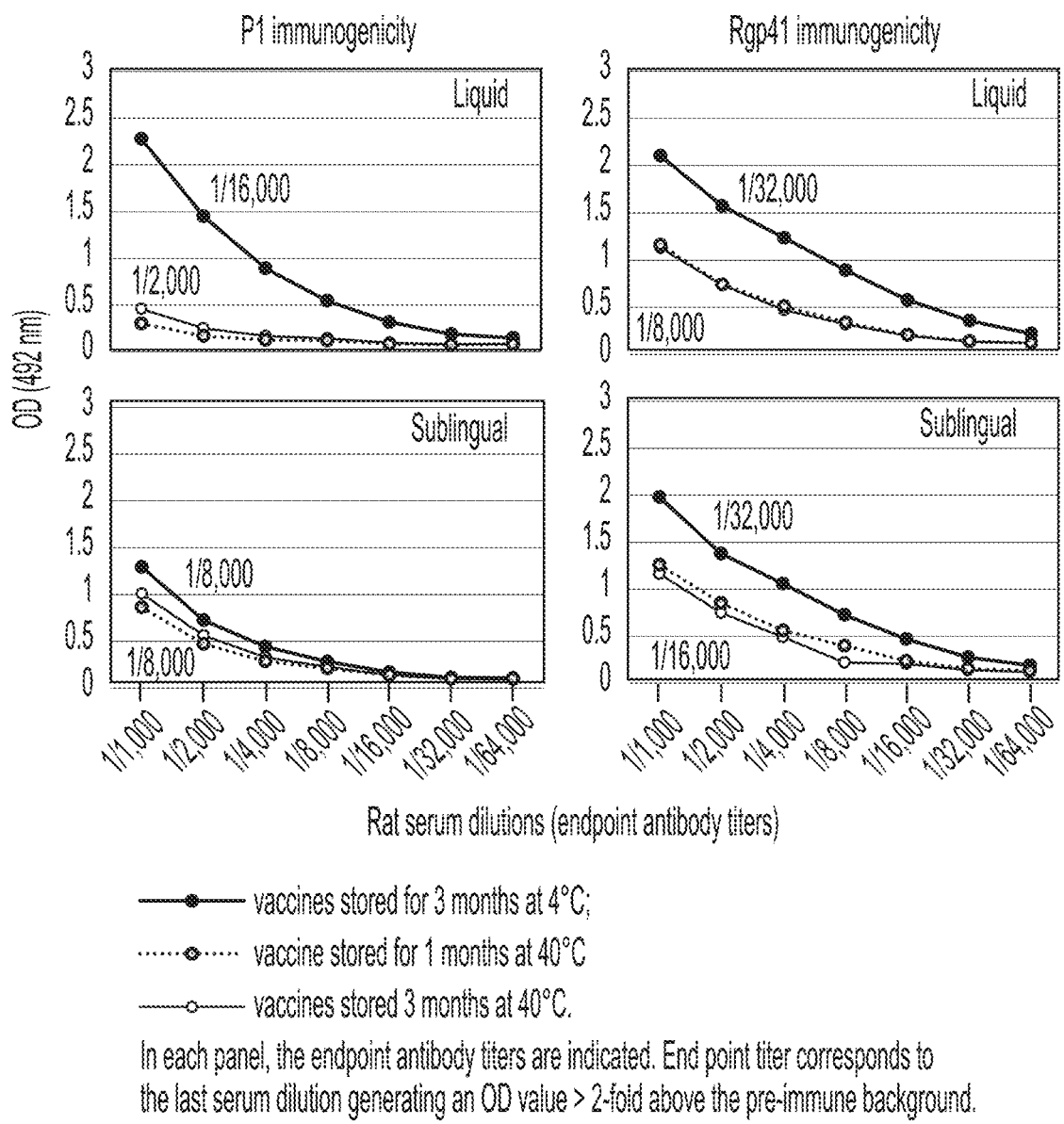
FIG. 5 illustrates the immunogenicity of P1 and rgp41 antigens of the liquid virosome concentrates and freeze-dried sublingual tablets containing virosomes, both stored at 4° C. and 40° C. over time.

Using semi-quantitative immunoblot analyses, antigens HIV-1 antigen P1 and rgp41 were monitored for degradations over 3 months. All samples were pre-diluted 2-fold. The human mAb 2F5 specific for P1 and the rabbit anti-rgp41 serum were used for this purpose. The liquid virosome concentrate batch MYM-V202 lot 170130-1 that was used to produce the vaccine batch was diluted 8-fold and used as a positive control. FIG. 4 shows a photo of the immunoblot analysis. For sample Z33787A101, tablets stored at 5° C. showed no or only a minimal decrease in the rgp41 antigen signal after 1 month and 3 months of storage compared to the initial sample (t=0). Similarly, there was only a minimal difference in the signal intensity for the unit stored at 25° C. for the rgp41 antigen, and a slight decrease for the P1 antigen. The difference for the 40° C. units was more pronounced, although this might still be within the assay accuracy of 10-20%.

The quantitative evaluation for the fluorescence data for rgp41 and P1 are presented in Tables 10 and 11, respectively. The upper part of each table shows the fluorescence raw data signal for each spot (from lowest to highest dilution) for the indicated stability sample. The lower part of each table shows the value for each sample spot compared to the respective dilution of the positive control spot (in % of the positive control). The bottom line shows the arithmetic average of all sample percentages. Obvious outliners of the measurements were excluded from the average calculation.

TABLE 10

| | | | Z33787A101 | | | | | |
|---|---|---|---|---|---|---|---|---|
| | | t = 0 | 1 month | | | 3 months | | |
| | MYM-V202 | 5° C. | 5° C. | 25° C. | 40° C. | 5° C. | 25° C. | 40° C. |
| rgp41 | 7702462 | 9058972 | 8032375 | 9201721 | 7801344 | 6321957 | 10300125 | 8521558 |
| | 4339215 | 5472388 | 4583281 | 4902260 | 4771430 | 4016424 | 4072924 | 3454675 |
| | 5371152 | 4467722 | 3785349 | 3403051 | 4176710 | 3596774 | 2556036 | 3084636 |
| | 3319677 | 3265426 | 2311220 | 3464764 | 3194101 | 3263683 | 3054427 | 2615003 |
| | 2259183 | 2179005 | 2166937 | 2708839 | 2159053 | 2482939 | 2704366 | 2043011 |
| | 1704534 | 1689938 | 1182171 | 1769144 | 1533427 | 1448772 | 1594263 | 1077611 |
| | 1339732 | 1048682 | 751850 | 1056018 | 675617 | 785497 | 976990 | 621839 |
| | 679095 | 632157 | 517094 | 514737 | 455636 | 490586 | 451385 | 417028 |
| | % of control | | 117.6 | 104.3 | 119.5 | 101.3 | 82.1 | 133.7 | 110.6 |
| | % of control | | 126.1 | 107.9 | 113.0 | 110.0 | 92.6 | 93.9 | 79.6 |
| | % of control | | 83.2 | 70.5 | 63.4 | 77.8 | 67.0 | 47.6 | 57.4 |
| | % of control | | 98.4 | 69.6 | 104.4 | 96.2 | 98.3 | 92.0 | 78.8 |
| | % of control | | 96.5 | 95.9 | 119.9 | 95.6 | 109.9 | 119.7 | 90.4 |
| | % of control | | 99.1 | 69.4 | 103.8 | 90.0 | 85.0 | 93.5 | 63.2 |
| | % of control | | 78.3 | 56.1 | 78.8 | 50.4 | 58.6 | 72.9 | 46.4 |
| | % of control | | 93.1 | 76.1 | 75.8 | 67.1 | 72.2 | 66.5 | 61.4 |
| | % (average) | | 99.0 | 81.2 | 97.3 | 86.0 | 74.0 | 80.0 | 65.3 |

TABLE 11

| | | | Z33787A101 | | | | | |
|---|---|---|---|---|---|---|---|---|
| | | t = 0 | 1 month | | | 3 months | | |
| | MVM-V202 | 5° C. | 5° C. | 25° C. | 40° C. | 5° C. | 25° C. | 40° C. |
| P1 | 2764625 | 1461965 | 1245932 | 1471586 | 1238537 | 1516476 | 1351413 | 1572627 |
| | 1208918 | 1606470 | 723609 | 1235559 | 1338350 | 547105 | 470287 | 508107 |
| | 845363 | 997068 | 578732 | 617270 | 997966 | 619197 | 352482 | 610820 |

TABLE 11-continued

| | | Z33787A101 | | | | | |
|---|---|---|---|---|---|---|---|
| | t = 0 | 1 month | | | 3 months | | |
| MVM-V202 | 5° C. | 5° C. | 25° C. | 40° C. | 5° C. | 25° C. | 40° C. |
| | 453354 | 904843 | 566560 | 879843 | 1200198 | 1211985 | 882260 | 490097 |
| | 249520 | 317945 | 287210 | 840751 | 673118 | 324793 | 339128 | 261055 |
| | 149361 | 269482 | 142741 | 311659 | 342849 | 146881 | 159835 | 115068 |
| | 86167 | 110800 | 63348 | 127920 | 163997 | 124010 | 91144 | 49784 |
| | 28407 | 42578 | 19915 | 18230 | 19079 | 24436 | 27082 | 27289 |
| % of control | 52.9 | 45.1 | 53.2 | 44.8 | 54.9 | 48.9 | 56.9 |
| % of control | 132.9 | 59.9 | 102.2 | 110.7 | 45.3 | 38.9 | 42.0 |
| % of control | 117.9 | 68.5 | 73.0 | 118.1 | 73.2 | 41.7 | 72.3 |
| % of control | 199.6 | 125.0 | 194.1 | 264.7 | 267.3 | 194.6 | 108.1 |
| % of control | 127.4 | 115.1 | 336.9 | 269.8 | 130.2 | 135.9 | 104.6 |
| % of control | 180.4 | 95.6 | 208.7 | 229.5 | 98.3 | 107.0 | 77.0 |
| % of control | 128.6 | 73.5 | 148.5 | 190.3 | 143.9 | 105.8 | 57.8 |
| % of control | 149.9 | 70.1 | 64.2 | 67.2 | 86.0 | 95.3 | 96.1 |
| % (average) | 136.2 | 81.6 | 147.6 | 161.9 | 112.4 | 96.0 | 76.8 |

For vaccine tablet for Z33787A101, tablets stored at 5° C. showed no or only a minimal decrease in the rgp41 and P1 antigens signal after 1 month and 3 months of storage compared to the initial sample (t=0). Similarly, there was only a minimal difference in the signal intensity for the unit stored at 25° C. for the rgp41 antigen, and a slight decrease for the P1 antigen. The difference for the 40° C. units was more pronounced for both antigens P1 and rpg41, although this might still be within the accuracy of the assay, especially since variations were seen within the serial dilution samples again.

Determination of 3M-052 was done by UV spectroscopy at 320 nm for all vaccine tablets stored at different temperatures of over 3 months. Values are presented in Tables 12 below.

TABLE 12

| Time point | Storage condition | OD (320 nm) |
|---|---|---|
| 0 | 5° C. | 0.116 |
| 1 month | 5° C. | 0.114 |
| 1 month | 25° C./60% RH | 0.112 |
| 1 month | 40° C./75% RH | 0.110 |

No discernible difference can be observed between these samples and therefore, 3M-052 concentrations were considered to remain stable in all samples within the accuracy of this assay. Overall, HA, P1, rpg41 and 3M-052 were stable in the freeze-dried tablets stored under different storage conditions, with minor variations over time as shown in Table 13 below.

TABLE 13

| Antigen and adjuvant detection during stability study | Liquid virosome concentrates | Freeze-dried tablets |
|---|---|---|
| Changes in rgp41 over 3 months at 5° C. (degradation not expected = reference) | Not significant | Not significant |
| Changes in rgp41 over 3 months at 25° C. (degradation), as compared to 5° C. | Not done | Minimal decrease |
| Changes in rgp41 over 3 months at 37-40° C. (degradation), as compared to 5° C. | Not done | Minimal decrease |
| Changes in P1 over 3 months at 5° C. (degradation not expected = reference) | Not significant | Not significant |
| Changes in P1 over 3 months at 25° C. (degradation), as compared to 5° C. | Not done | Minimal decrease |
| Changes in P1 over 3 months at 37-40° C. (degradation), as compared to 5° C. | Not done | Minimal decrease |
| Changes in 3 M-052 over 3 months at 5° C. (degradation not expected = reference) | Not significant | Not significant |
| Changes in 3 M-052 over 3 months at 37-40° C. (degradation), as compared to 5° C. | Not significant | Not significant |

Example 3: Stability Data of Freeze-Dried Vaccine Dosage Forms (Formulation 2) Stored Under ICH Conditions The stability of the virosome vaccine in the form of a freeze-dried tablet for Formulation 2 is illustrated in this example. Liquid virosome concentrate batch MYM V202 lot 17MYM002/F17255 supplied by Mymetics comprising of approximately 121 µg/ml HIV-1 P1, 67 µg/ml HIV-1 rgp41, 41 µg/ml HA (A/Brisbane/59/2007 (H1N1), 39 µg/ml adjuvant 3M-052 in HN buffer pH 7.4 (50 mM HEPES, 142.5 mM NaCl) with 7% w/w trehalose was used for the manufacture of lyophilized vaccine tablets (batch MYM-212 lot 1690747).

To prepare the vaccine tablet, a liquid virosome formulation mix was prepared first. It contained 25% w/w of liquid virosome concentrate batch MYM V202 lot 17MYM002/F17255, 6% w/w fish gelatin, 8% w/w mannitol, 2% w/w (net) trehalose, sodium hydroxide solution (quantum satis) to pH 7.4, and purified water (quantum satis) to 100% w/w.

The liquid virosome formulation mixture was dosed with a 500 mg dosing fill weight aliquot at 15° C. into blister pockets of aluminum trays. The trays containing the dosed aqueous vaccine mix were frozen by passing the trays through a freezing chamber set at −70° C. for a duration of 3 minutes 15 seconds. The aluminium trays containing the frozen products were collected and placed in a freezer at a temperature of <−15° C. A 2-step FD cycle using −15° C. for 24 hours followed by −10° C. for 18 hours was then used.

The blisters of freeze-dried tablets were sealed in sachets and placed on storage for 3 months at 5° C., 25° C./60% relative humidity, and 40° C./75 relative humidity. The results at initial testing and at 6 months testing are summarized in Table 14 below.

TABLE 14

| Test | Appearance | Disintegration Time | Moisture Content |
|---|---|---|---|
| Initial | Good | 22 seconds | 3.6% |
| 1 month at 5° C. | Good | 8 seconds | 3.8% |
| 1 month at 25° C./60% RH | Good | 16 seconds | 3.7% |
| 1 month at 40° C./75% RH | Good | 14 seconds | 3.6% |
| 3 months at 5° C. | Good | 12 seconds | 3.7% |
| 3 months at 25° C./60% RH | Good | 10 seconds | 3.7% |
| 3 months at 40° C./75% RH | Good | 13 seconds | 3.9% |
| 6 months at 5° C. | Good | 8 seconds | 3.9% |
| 6 months at 25° C./60% RH | Good | 10 seconds | 3.8% |
| 6 months at 40° C./75% RH | Good | 13 seconds | 4.0% |

The stability data shows that the tablet appearance was good and consistent between batches. The moisture content was 3.6-4.0% w/w with little difference between the different stability conditions over the 6-month storage period. As this formulation contains 8% w/w mannitol, there is less microstructural collapse during freeze drying as indicated in the shorter and more consistent disintegration times.

The stability of the antigens content (HIV-1 antigen P1 and rgp41) were monitored for degradations over 3 months using HPLC assay). For the liquid vaccine MYM V202 (starting material), it was found that that the P1 content was reduced by 4% and 7% when stored at 2-8° C. (cold storage condition) for 1 month and 3 months respectively. For rgp41, the content was reduced by 16% and 25% at 1 and 3 months respectively at cold storage condition. When the liquid virosome was stored at 25° C. and 40° C., P1 and rgp41 were no longer detected after 1 month and 3 months.

The results of the antigen contents in the lyophilised tablet on storage are presented in Table 15 and Table 16 for antigen P1 and antigen rgp41 respectively. In the lyophilised tablet form, the P1 antigen remained very stable without observed content decline after 3 months at 2-8° C. (cold chain condition) and also remained in unaffected during 1 and 3 months storage outside the cold chain condition. For the rgp41 antigen, a decline of about 5%, 10% and 20% was observed after 1 months at 2 −8° C., 25° C. and 40° C. respectively. At 3 months storage, the decline was about 13%, 15% and 19% respectively. Taken into consideration of the HPLC method accuracy, an observed decline concentration difference of less the 15% are not significant. Furthermore, the observed gradual antigen loss or decline is related to chemical modifications and not due to advanced degradation with structural cleavage, amino acid loses or aggregation. Meanwhile, chemical modification(s) in a given epitope may potentially alter its recognition, decreasing or increasing antibodies binding toward that region, while other regions would remain equally well recognized.

At T0, P1 and rgp41 antigens harbour similar SDS-PAGE migration profile and were still recognized by specific monoclonal antibodies, once under sublingual tablets, and serum antibodies toward P1 and rgp41 were still reacting toward various P1 and gp41 peptides harbouring key epitopes. These analyses suggest that in overall, P1 and rgp41 have preserved most of their antigenicity and immunogenicity during the manufacturing process (data not shown).

TABLE 15

| | P1 content (lyophilized tablet) | | |
|---|---|---|---|
| Time point | μg/ml | μg/unit | % reduction/increase |
| Storage at 2-8° C. (average 5° C.) (cold chain condition) | | | |
| Initial (T0) | 24.7 | 12.35 | Not applicable |
| 1 month (T1) | 28.6 | 14.3 | +15.8 (no lost) |
| 3 months (T3) | 27.6 | 13.8 | +11.7 (no lost) |
| Storage at 25° C./60% RH | | | |
| 1 month (T1) | 27.9 | 13.95 | +13.0 (no lost) |
| 3 months (T3) | 27.5 | 13.75 | +11.13 (no lost) |
| Storage at 40° C./75% RH | | | |
| 1 month (T1) | 25.8 | 12.9 | +4.5 (no lost) |
| 3 months (T3) | 24.0 | 12.0 | −2.8 (lost) |

TABLE 16

| | rgp41 content (lyophilized tablet) | | |
|---|---|---|---|
| Time point | μg/ml | μg/unit | % reduction |
| Storage at 2-8° C. (average 5° C.) (cold chain condition) | | | |
| Initial (T0) | 13.5 | 6.75 | Not applicable |
| 1 month (T1) | 12.8 | 6.4 | −5.2 |
| 3 months (T3) | 11.8 | 5.9 | −12.6 |
| Storage at 25° C./60% RH | | | |
| 1 month (T1) | 12.1 | 6.05 | −10.4 |
| 3 months (T3) | 11.5 | 5.75 | −14.8 |
| Storage at 40° C./75% RH | | | |
| 1 month (T1) | 10.8 | 5.4 | −20.0 |
| 3 months (T3) | 10.9 | 5.45 | −19.3 |

Example 4: Stability of Lyophilized Tablets Stored Under Sub-Zero Temperature Storage Conditions The data in Example 4 shows the stability of the physical characteristics of the virosome vaccine tablets and the virosome particles when stored under sub-zero conditions. A liquid virosome formulation mix containing 25% w/w loading of liquid virosomes concentrate MYM-201 lot 160125-1 supplied by Mymetics (containing HA 70-80 µg/ml, P1 40-50 µg/ml, rgp41 70-80 µg/ml (A/Brisbane/59/2007 (H1N1) in HN buffer pH 7.4 (50 mM HEPES, 142.5 mM NaCl), 6% w/w fish gelatin, 8% w/w mannitol, and 2% w/w (net) trehalose was dosed with a 500 mg dosing fill weight and freeze dried. The formulations were dosed with a 500 mg dosing fill weight aliquot at 15° C. into blister pockets of aluminum trays. The trays containing the dosed aqueous vaccine mix were frozen by passing the aluminium trays through a freezing chamber set at −70° C. for a duration of 3 minutes 15 seconds. The aluminium trays containing the frozen products were collected and placed in a freezer at a temperature of <−15° C. and annealed for 6 hours frozen hold before lyophilisation. A 2-step FD cycle using −15° C. for 24 hours followed by −10° C. for 18 hours was then used. The blisters of freeze-dried tablets were sealed in sachets and were placed on storage in a freezer at −15° C. for 1 week. A corresponding set of blisters of tablets were sealed in sachets and were placed at ambient conditions for the same durations. These tablets were assessed for appearance, dispersion characteristics (wetting time and dissociation time) and virosome particle size distribution as described according to the test methods above.

All units were found to have good appearance after storage at both conditions. The data showed that sub-zero storage had little effect on the tablet dispersion characteristics (wetting and dissociation times) (Table 17) and virosome particle size distribution (Table 18).

TABLE 17

| Condition | Wetting Time (sec) | Dissociation Time (sec) |
|---|---|---|
| Ambient Storage | <31 | <37 |
| Sub-Zero Storage | <32 | <35 |

TABLE 18

| Condition | NTA: Main Peak Particle Size (nm) | NTA: % virosome particle (<200 nm) |
|---|---|---|
| 1 week ambient Post-Digestion | 130 | 59.9 |
| 1 week Sub-Zero, Post-Digestion | 132 | 60.6 |

Example 5: Flow Cytometry Assessment of Virosome Particles from Reconstituted Freeze-Dried Tablets Estimations of virosome proportions preserved in freeze-dried tablet samples from process development is summarised below. The values provided in Table 19 were derived from AMNIS flow cytometry data using measurements of events in the focus area corresponding to the virosome gates.

TABLE 19

| Vaccine formulation | Percentage of virosome recovered from end of production | Percentage of clusters (doublets, triplets, higher forms) |
|---|---|---|
| Liquid vaccine | 100% | <5% |
| Freeze-dried tablet (reconstitutes | 24-40% | 10-25% |

The data shows that 24-40% of the starting virosome is preserved in the freeze-dried tablets of which between 10-25% of these virosomes are in clusters, mostly as doublets and triplets.

Example 6: Immunogenicity Evaluation of P1 and Rgp41 Antigens from Liquid Virosome Formulation and Reconstituted Freeze Dried Sublingual Tablets Containing Virosome Liquid virosome concentrates (liquid vaccine MYM-V202) and freeze-dried sublingual tablets containing virosome for Example 3 and placed on storage at 4° and 40° C. over a period of three months for immunogenicity assessment. After storage for 1 month, samples of the liquid vaccine and sublingual tablets stored at 40° C. were removed for the storage cabinet for immunogenicity assessment. After storage for 3 months, samples of the liquid vaccine and sublingual tablets stored at 4° C. and 40° C. were removed for immunogenicity assessment.

For the immunogenicity assessment, Wistar rats (n=10 per group), 50% of each gender were used. The rats were immunized at day 0, day 28 and day 56. The liquid vaccine contained 3.9 μg of P1, 2.2 μg of rgp41 and 1.3 μg of 3M-052 TLR7/8 (adjuvant) in 0.1 mL and this was used for subcutaneous injection. For the sublingual tablets, an adequate quantity of sublingual tablet was dissolved in sterile water to achieve about 3 μg of P1, 1.7 μg of rgp41 and 1 μg of 3M-052 TLR7/8 (adjuvant) in 0.1 mL to be administered by subcutaneous injection. Pre-immune serums were collected at day 0 and immune serums at day 65 for determining the end point antibody titers for each animal serums and on the serum pool.

FIG. 5 shows the immunogenicity of P1 and rgp41 from the liquid vaccine and sublingual tablets stored at different temperatures. The liquid adjuvanted vaccine formulation MYM-V202 containing both P1 and rgp41 antigens were temperature sensitive and served as reference material for comparison with the immunogenicity of the sublingual tablet vaccine form with improve thermostability. (Black line) shows vaccines stored for 3 months at 4° C.; (Black dash line) shows vaccine stored for 1 month at 40° C.; (Grey line) shows vaccines stored for 3 months at 40° C. The data shows that the immunogenicity of the antigens for the freeze-dried tablets are retained. In each panel, the endpoint antibody titers are also indicated. End point titer corresponds to the last serum dilution generating an OD value >2-fold above the pre-immune background.

Additional Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

Reference to "about" a value or parameter herein includes (and describes) variations that are directed to that value or parameter per se. For example, description referring to "about X" includes description of "X". In addition, reference to phrases "less than", "greater than", "at most", "at least", "less than or equal to", "greater than or equal to", or other similar phrases followed by a string of values or parameters is meant to apply the phrase to each value or parameter in the string of values or parameters. For example, a statement that a solution has a concentration of at least about 10 mM, about 15 mM, or about 20 mM is meant to mean that the solution has a concentration of at least about 10 mM, at least about 15 mM, or at least about 20 mM.

As used herein, the singular forms "a," "an," and "the" are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

This application discloses several numerical ranges in the text and figures. The numerical ranges disclosed inherently support any range or value within the disclosed numerical ranges, including the endpoints, even though a precise range limitation is not stated verbatim in the specification because this disclosure can be practiced throughout the disclosed numerical ranges.

The above description is presented to enable a person skilled in the art to make and use the disclosure, and is provided in the context of a particular application and its requirements. Various modifications to the preferred embodiments will be readily apparent to those skilled in the art, and the generic principles defined herein may be applied to other embodiments and applications without departing from the spirit and scope of the disclosure. Thus, this disclosure is not intended to be limited to the embodiments shown, but is to be accorded the widest scope consistent with the principles and features disclosed herein.

The invention claimed is:

1. An oral solid vaccine dosage form comprising:
    lipid-based vesicles comprising an immunogenic amount of at least one target molecule;
    5-20 wt. % of at least one cryo-lyoprotectant;
    25-40 wt. % of a matrix former; and
    40-55 wt. % of a structure former.
2. The dosage form of claim 1, wherein the lipid-based vesicles are virosomes or proteoliposomes.
3. The dosage form of claim 1, wherein the dosage form comprises 10-15 wt. % of at least one cryo-lyoprotectant.
4. The dosage form of claim 1, wherein the at least one cryo-lyoprotectant comprises trehalose.
5. The dosage form of claim 1, wherein the dosage form comprises 33-37 wt. % of the matrix former.
6. The dosage form of claim 1, wherein the matrix former comprises gelatin.
7. The dosage form of claim 6, wherein the gelatin comprises fish gelatin.
8. The dosage form of claim 7, wherein the fish gelatin is high molecular weight fish gelatin.
9. The dosage form of claim 1, wherein the dosage form comprises 45-50 wt. % of the structure former.
10. The dosage form of claim 1, wherein the structure former comprises mannitol.
11. The dosage form of claim 1, wherein the virosomes are derived from the influenza virus membrane or other enveloped viruses.
12. The dosage form of claim 1, wherein the at least one target molecule is present on the virosome.
13. The dosage form of claim 1, wherein the at least one target molecule comprises an HIV-1 envelope derived antigen.
14. The dosage form of claim 13, wherein the HIV-1 envelope derived antigen comprises HIV-1 PI peptide and/or HIV-1 recombinant gp41.
15. The dosage form of claim 1, wherein the virosomes comprise adjuvant.
16. The dosage form of claim 1, wherein the dosage form is configured to disintegrate in an oral cavity to facilitate oral cavity uptake of the at least one target molecule.
17. The dosage form of claim 16, wherein the dosage form is configured to disintegrate within 180 seconds after being placed in the oral cavity.
18. The dosage form of claim 16, wherein the dosage form is configured to disintegrate within 90 seconds after being placed in the oral cavity.
19. The dosage form of claim 16, wherein the dosage form is configured to disintegrate within 60 seconds after being placed in the oral cavity.
20. The dosage form of claim 16, wherein the dosage form is configured to disintegrate within 30 seconds after being placed in the oral cavity.
21. The dosage form of claim 16, wherein the dosage form is configured to induce an immune response when administered to a patient by placement in the oral cavity.
22. The dosage form of claim 21, wherein placement in the oral cavity is placement on or under the tongue or in the buccal or pharyngeal region.
23. A method of inducing an immune response in a patient, the method comprising placing the dosage form of claim 1 in an oral cavity of a person in need of the immune response.
24. The method of claim 23, wherein placement in the oral cavity is placement on or under the tongue or in the buccal or pharyngeal region.
25. A method of forming an oral solid vaccine dosage form, the method comprises:
    dosing a liquid virosome formulation into a preformed mold, wherein the virosome formulation comprises:
        lipid-based vesicles comprising an immunogenic amount of at least one target molecule;
        1-5 wt. % of a cryo-lyoprotectant;
        4-8 wt. % of a matrix former; and
        5-10 wt. % of a structure former;
    freezing the dosed virosome formulation at a temperature of −60° C. to −90° C.;
    annealing the frozen virosome formulation by holding it at a temperature of less than −15° C. for 3-9 hours; and
    freeze-drying the annealed virosome formulation to form the dosage form.
26. The method of claim 25, wherein the dosed virosome formulation is frozen at a temperature of −60° C. to −90° C. for a duration of about 1-5 minutes.
27. The method of claim 25, wherein freeze-drying the annealed virosome formulation comprises a first step of holding the annealed virosome formulation at a temperature of −10° C. to −20° C. for 20-28 hours and a second step of holding the annealed virosome formulation at a temperature of −5° C. to about −15° C. for 14-22 hours.

28. The method of claim 25, wherein the freeze-drying occurs at a pressure of less than 600 mbar.

29. The method of claim 25, wherein the virosome formulation has a pH of about 6.5-8.

30. The method of claim 25, wherein the cryo-lyoprotectant comprises trehalose.

31. The method of claim 25, wherein the matrix former comprises gelatin.

32. The method of claim 31, wherein the gelatin comprises fish gelatin.

33. The method of claim 32, wherein the fish gelatin is high molecular weight fish gelatin.

34. The method of claim 25, wherein the structure former comprises mannitol.

35. The method of claim 25, wherein the lipid-based vesicles are derived from the influenza virus or respiratory syncytial virus.

36. The method of claim 25, wherein the at least one target molecule comprises an HIV-1 envelope derived antigen.

37. The method of claim 36, wherein the HIV-1 envelope derived antigen comprises HIV-1 PI peptide and/or HIV-1 recombinant gp41.

38. The method of claim 25, wherein the lipid-based vesicles comprise adjuvant.

39. A method of forming an oral solid vaccine dosage form, the method comprises:
  dosing a liquid virosome formulation into a preformed mold, wherein the virosome formulation comprises:
    20-50 wt. % of a virosome concentrate, wherein the virosome concentrate comprises:
      virosomes comprising an immunogenic amount of at least one target molecule;
      2-10 wt. % of a cryo-lyoprotectant; and
      60-200 mM of a buffer system;
    4-8 wt. % of a matrix former; and
    5-10 wt. % of a structure former;
  freezing the dosed virosome formulation at a temperature of −60° C. to −80° C.;
  annealing the frozen virosome formulation by holding it at a temperature of less than −15° C. for 3-9 hours; and
  freeze-drying the annealed virosome formulation to form the dosage form.

40. The method of claim 39, wherein the buffer system comprises HEPES-Sodium Chloride.

* * * * *